United States Patent
Ueda

(10) Patent No.: US 10,932,879 B2
(45) Date of Patent: Mar. 2, 2021

(54) MEDICAL OBSERVATION APPARATUS AND STATE NOTIFICATION METHOD

(71) Applicant: Sony Olympus Medical Solutions Inc., Tokyo (JP)

(72) Inventor: Masaaki Ueda, Kanagawa (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 540 days.

(21) Appl. No.: 15/923,098

(22) Filed: Mar. 16, 2018

(65) Prior Publication Data

US 2018/0296294 A1    Oct. 18, 2018

(30) Foreign Application Priority Data

Apr. 13, 2017   (JP) .............................. JP2017-080007

(51) Int. Cl.

| A61B 46/10 | (2016.01) |
| G06T 7/70 | (2017.01) |
| G02B 21/00 | (2006.01) |
| A61B 90/20 | (2016.01) |
| G02B 21/36 | (2006.01) |
| A61B 90/50 | (2016.01) |
| A61B 90/25 | (2016.01) |
| G02B 7/00 | (2021.01) |
| A61B 90/00 | (2016.01) |
| G06T 7/20 | (2017.01) |

(52) U.S. Cl.
CPC .............. *A61B 46/10* (2016.02); *A61B 90/20* (2016.02); *A61B 90/25* (2016.02); *A61B 90/361* (2016.02); *A61B 90/50* (2016.02); *G02B 7/001* (2013.01); *G02B 21/362* (2013.01); *G06T 7/20* (2013.01); *G06T 7/70* (2017.01); *A61B 2090/061* (2016.02); *A61B 2090/373* (2016.02); *G02B 21/0012* (2013.01)

(58) Field of Classification Search
CPC ........... G06T 7/0012; G06T 7/20; G06T 7/70; G01B 7/14; G01B 11/14; G01B 21/16; G02B 21/0012; G02B 21/362; A16B 2090/061; A16B 90/20; A16B 90/25; A16B 90/361; A16B 2090/373
See application file for complete search history.

(56) References Cited

U.S. PATENT DOCUMENTS

2020/0253683 A1*   8/2020 Amanatullah et al. .....................
                                                                G16H 50/30

FOREIGN PATENT DOCUMENTS

JP            2016-7233 A      1/2016

* cited by examiner

*Primary Examiner* — Andrew W Johns
(74) *Attorney, Agent, or Firm* — Xsensus LLP

(57) ABSTRACT

There is provided a medical observation apparatus including: a determination section configured to determine, on a basis of distance between a part corresponding to a sterile region and an object existing in a periphery of the part corresponding to the sterile region, if an approaching state in which an object is approaching the part corresponding to the sterile region exists; and a notification control section configured to cause a notification of the approaching state to be issued, on a basis of a determination result of the approaching state.

16 Claims, 10 Drawing Sheets

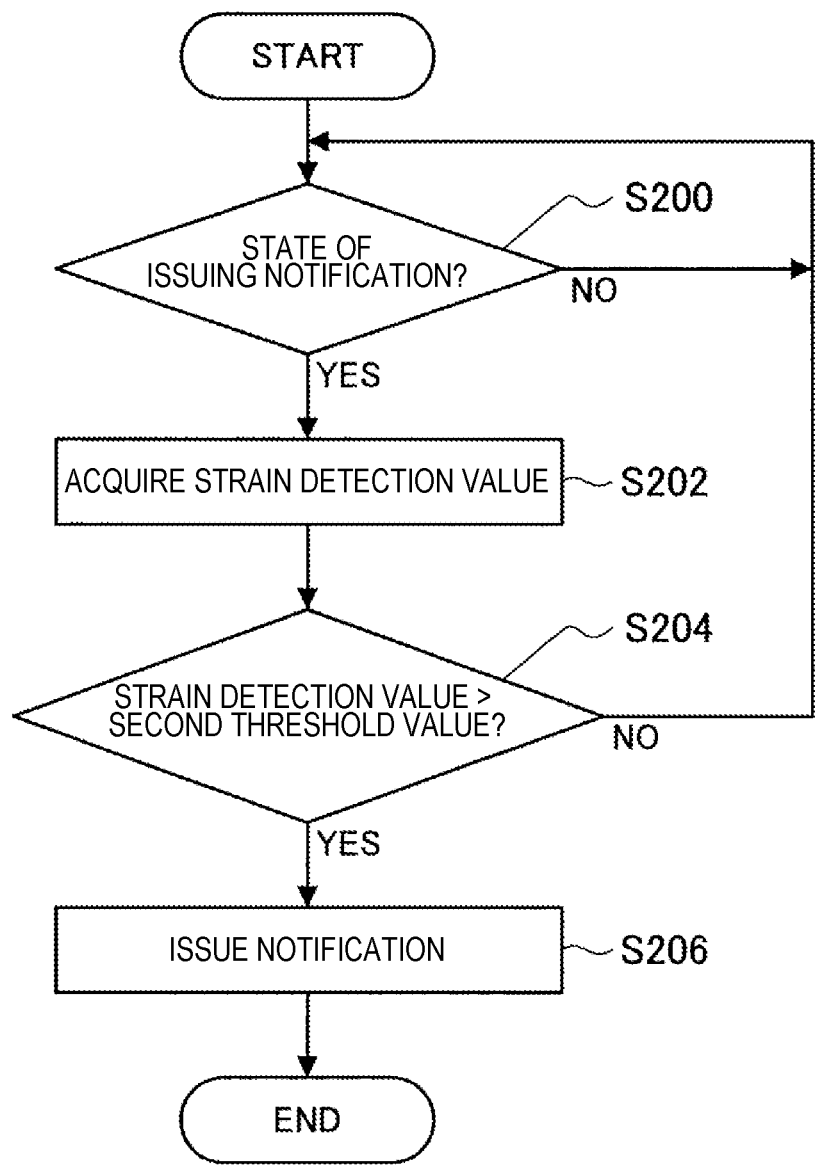

MEDICAL OBSERVATION APPARATUS AND STATE NOTIFICATION METHOD

CROSS REFERENCE TO RELATED APPLICATIONS

This application claims the benefit of Japanese Priority Patent Application JP 2017-080007 filed Apr. 13, 2017, the entire contents of which are incorporated herein by reference.

BACKGROUND

The present disclosure relates to a medical observation apparatus and a state notification method.

Recently, in the medical field, to support microsurgery such as neurosurgical procedures, for example, medical observation apparatus capable of enlarged observation of an observation target such as an affected area are used in some cases. Examples of medical observation apparatus include a medical observation apparatus provided with an optical microscope, and a medical observation apparatus provided with an imaging device that functions as an electronic imaging microscope. In the following, the above medical observation apparatus provided with an optical microscope will be designated an "optical medical observation apparatus". Also, in the following, the above medical observation apparatus provided with an imaging device will be designated an "electronic imaging medical observation apparatus" or simply a "medical observation apparatus" in some cases.

Also, to ensure a sterile state, optical medical observation apparatus and electronic imaging medical observation apparatus are often used while being covered by a medical sterile cover called a drape. In these circumstances, technology related to medical sterile covers is being developed. Examples of the above technology include the technology described in JP 2016-7233A.

SUMMARY

As described above, to ensure a sterilized state, optical medical observation apparatus and electronic imaging medical observation apparatus are often used while being covered by a medical sterile cover. In optical medical observation apparatus and electronic imaging medical observation apparatus, the part covered by the medical sterile drape becomes a region (hereinafter designated the "sterile region") where a sterile state is ensured.

If a site whose sterile state is not ensured, such as the face or head of a medical personnel member, comes into contact with the sterile region, the medical personnel member may need to re-cover the optical medical observation apparatus or electronic imaging medical observation apparatus with a new medical sterile cover. If a situation of re-covering with a new medical sterile cover like the above occurs, surgery is interrupted temporarily, which leads to reduced surgical efficiency. Additionally, increased costs due to the use of a new medical sterile cover are a concern.

The present disclosure proposes a novel and improved medical observation apparatus and state notification method, by which contact with a sterile region by a medical personnel member can be preemptively deterred.

According to an embodiment of the present disclosure, there is provided a medical observation apparatus including: a determination section configured to determine, on a basis of distance between a part corresponding to a sterile region and an object existing in a periphery of the part corresponding to the sterile region, if an approaching state in which an object is approaching the part corresponding to the sterile region exists; and a notification control section configured to cause a notification of the approaching state to be issued, on a basis of a determination result of the approaching state.

In addition, according to an embodiment of the present disclosure, there is provided a state notification method executed by a medical observation apparatus, the state notification method including: determining, on a basis of distance between a part corresponding to a sterile region and an object existing in a periphery of the part corresponding to the sterile region, if an approaching state in which an object is approaching the part corresponding to the sterile region exists; and causing a notification of the approaching state to be issued, on a basis of a determination result of the approaching state.

According to an embodiment of the present disclosure, contact with a sterile region by a medical personnel member can be preemptively deterred.

Note that the effects described above are not necessarily limitative. With or in the place of the above effects, there may be achieved any one of the effects described in this specification or other effects that may be grasped from this specification.

BRIEF DESCRIPTION OF THE DRAWINGS

FIG. 10 is a flowchart illustrating another example of a process related to the state notification method according to the present embodiment.

DETAILED DESCRIPTION OF THE EMBODIMENT(S)

Figure 1:
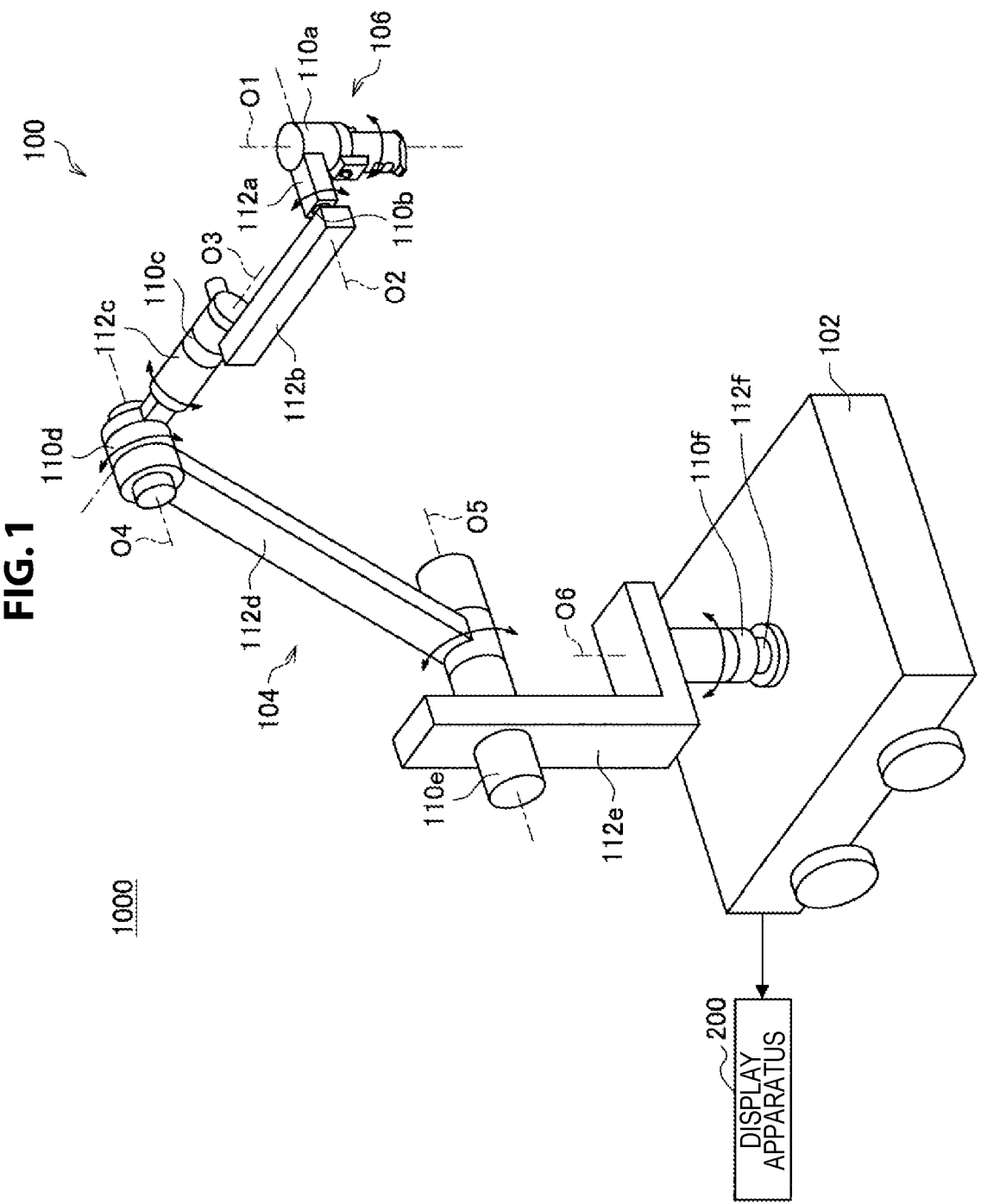
FIG. 1 is an explanatory diagram illustrating an example of a configuration of a medical observation system according to the present embodiment.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

The description hereinafter will proceed in the following order.

1. Medical observation system according to present embodiment and state notification method according to present embodiment
2. Program according to present embodiment (Medical Observation System According to Present Embodiment and State Notification Method According to Present Embodiment)

Hereinafter, an example of a medical observation system according to the present embodiment will be described, while a state notification method according to the present embodiment will also be described.

Note that although the following mainly gives an example of a case in which the medical observation apparatus according to the present embodiment is an electronic imaging medical observation apparatus, the medical observation apparatus according to the present embodiment is not limited to an electronic imaging medical observation apparatus. For example, the medical observation apparatus according to the present embodiment may also be an optical medical observation apparatus. Even in the case in which the medical observation apparatus according to the present embodiment is an optical medical observation apparatus, the state notification method according to the present embodiment described later is still applicable.

[1] Configuration of Medical Observation System

FIG. 1 is an explanatory diagram illustrating an example of the configuration of a medical observation system 1000 according to the present embodiment. The medical observation system 1000 includes a medical observation apparatus 100 and a display apparatus 200, for example.

Note that the medical observation system according to the present embodiment is not limited to the example illustrated in FIG. 1.

For example, the medical observation system according to the present embodiment additionally may include a control apparatus (not illustrated) that controls various operations in the medical observation apparatus 100. In the medical observation system 1000 illustrated in FIG. 1, as described later, an example is illustrated in which, by providing the medical observation apparatus 100 with a control section (described later) that performs processes according to the state notification method according to the present embodiment, the medical observation apparatus 100 includes the functions of the control apparatus (not illustrated).

Examples of the control apparatus (not illustrated) include arbitrary equipment capable of performing processes according to the state notification method according to the present embodiment, such as a "medical controller" and a "computer such as a server". Also, the control apparatus (not illustrated) may be, for example, an integrated circuit (IC) that can be embedded in equipment like the above.

Additionally, the medical observation system according to the present embodiment may also be a configuration that includes multiple medical observation apparatuses 100 and display apparatuses 200. In the case of including multiple medical observation apparatuses 100, in each medical observation apparatus 100, processes according to the state notification method in the medical observation apparatus 100 described later are performed. Also, in the case in which the medical observation system according to the present embodiment is a configuration that includes multiple medical observation apparatuses 100 and display apparatuses 200, the medical observation apparatus 100 and the display apparatus 200 may be associated in a 1-to-1 manner, or multiple medical observation apparatuses 100 may be associated with a single display apparatus 200. In the case in which multiple medical observation apparatuses 100 are associated with a single display apparatus 200, which medical observation apparatus 100 provides a taken image to be displayed on a display screen is switched by performing a switching operation or the like in the display apparatus 200, for example.

Figure 2:
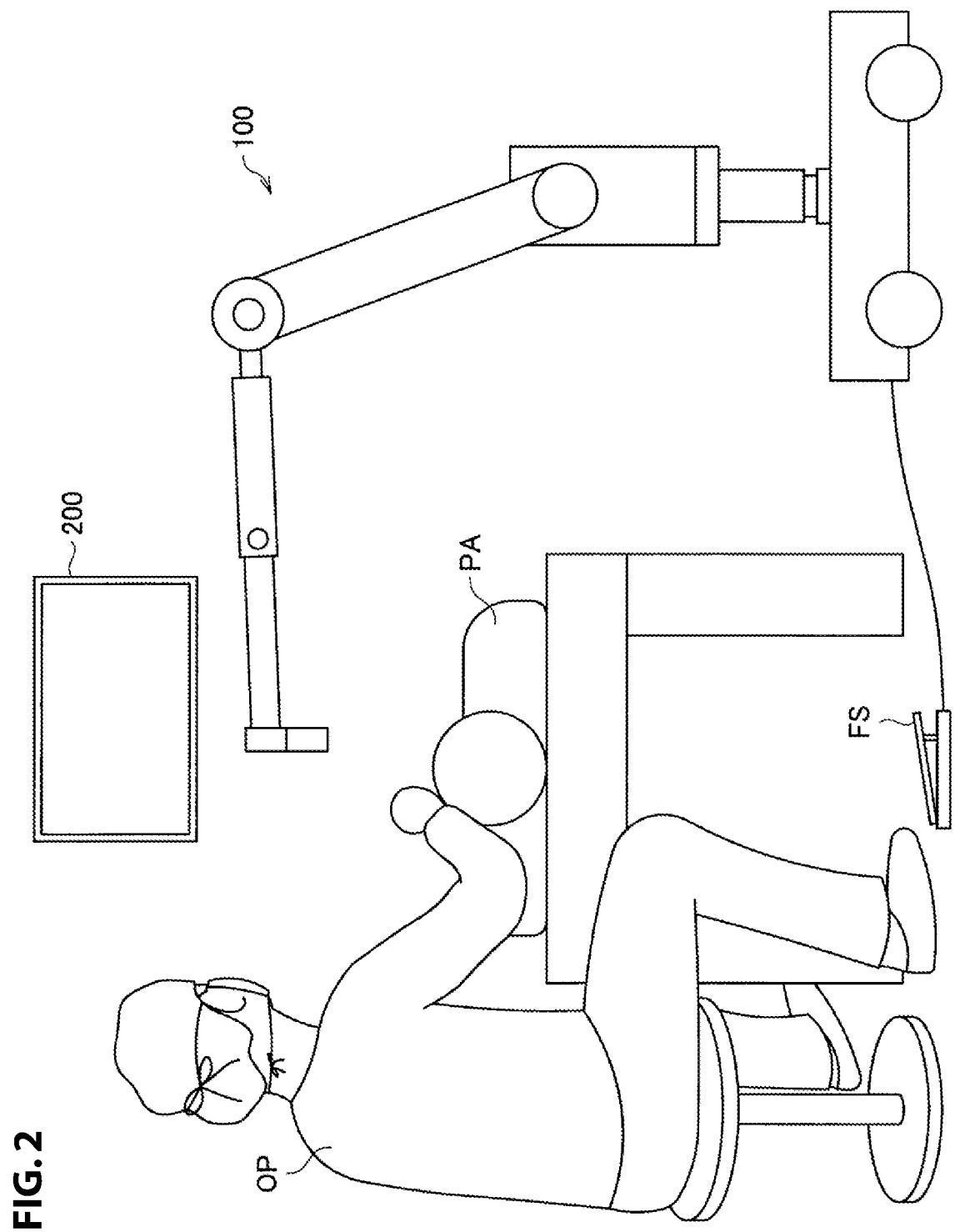
FIG. 2 is an explanatory diagram illustrating an example of a use case in which the medical observation system according to the present embodiment is used.

FIG. 2 is an explanatory diagram illustrating an example of a use case in which the medical observation system 1000 according to the present embodiment is used.

By an imaging device (described later) provided in the medical observation apparatus 100, an observation target patient PA (a patient who undergoes a medical procedure) is imaged. In the following, a captured image captured by the medical observation apparatus according to the present embodiment, such as a captured image that captures the above patient who undergoes a medical procedure, is designated a "medical captured image".

The medical captured image captured in the medical observation apparatus 100 is displayed on a display screen of a display apparatus 200. Subsequently, a surgeon OP (an example of a user of the medical observation apparatus 100) who performs a medical procedure by using the medical observation apparatus 100 performs the medical procedure on the patient PA while looking at the medical captured image displayed on the display screen of the display apparatus 200.

Also, the surgeon OP operates an operating device external to the medical observation apparatus 100, such as a footswitch FS, or an operating device (described later) provided in the medical observation apparatus 100, thereby causing an arm (described later) and the imaging device (described later) provided in the medical observation apparatus 100 to operate, and putting the medical observation apparatus 100 into a desired state.

Hereinafter, each apparatus included in the medical observation system 1000 will be described.

[1-1] Display Apparatus 200

The display apparatus 200 is a display device in the medical observation system 1000, and corresponds to an external display device from the perspective of the medical observation apparatus 100. The display apparatus 200 displays various images on a display screen, such as a medical captured image (a moving image or multiple still images; the same applies hereinafter) taken in the medical observation apparatus 100, or an image related to a user interface (UI), for example. In addition, the display apparatus 200 may also be a configuration capable of 3D display. The display on the display apparatus 200 is controlled by, for example, the medical observation apparatus 100 or the control apparatus (not illustrated).

In the medical observation system 1000, the display apparatus 200 is installed in an arbitrary location visible to a person involved in a surgery inside an operating room, such as on a wall, the ceiling, or the floor of the operating room, for example. Examples of the display apparatus 200 include a liquid crystal display, an organic electro-luminescence (EL) display, a cathode ray tube (CRT) display, and the like.

Note that the display apparatus 200 is not limited to the example illustrated above.

For example, the display apparatus 200 may also be an arbitrary wearable apparatus that is used by being worn on the body of the surgeon or the like, such as a head-mounted display, an eyewear-type apparatus, or the like.

The display apparatus 200 runs on electric power supplied from an internal power source such as a battery provided in the display apparatus 200, on electric power supplied from a connected external power source, or the like, for example.

[1-2] Medical Observation Apparatus 100

The medical observation apparatus 100 is an electronic imaging medical observation apparatus. For example, in the case in which the medical observation apparatus 100 is used during surgery, the surgeon (one example of the user of the medical observation apparatus 100) observes an operating site while referring to a medical captured image which has been taken by the medical observation apparatus 100 and displayed on the display screen of the display apparatus 200, and performs various treatments, such as techniques depending on the surgical procedure, on the operating site.

First, FIG. 1 will be referenced to describe an example of a hardware configuration of the medical observation apparatus 100.

The medical observation apparatus 100 is provided with a base 102, an arm 104, an imaging device 106, and sensors (a sensor group), for example. Additionally, although not illustrated in FIG. 1, the medical observation apparatus 100 may also be provided with, for example, one or multiple processors (not illustrated) including a computational circuit such as a microprocessing unit (MPU), read-only memory (ROM; not illustrated), random access memory (RAM; not illustrated), a recording medium (not illustrated), and a communication device (not illustrated). The medical observation apparatus 100 runs on electric power supplied from an internal power source such as a battery provided in the medical observation apparatus 100, on electric power supplied from a connected external power source, or the like, for example.

The one or multiple processors (not illustrated) function as the control section described later. The ROM (not illustrated) stores programs and control data such as computational parameters used by the one or multiple processors (not illustrated). The RAM (not illustrated) temporarily stores programs executed by the one or multiple processors (not illustrated), or the like.

The recording medium (not illustrated) functions as a storage section described later. A variety of data is stored on the recording medium (not illustrated), including data related to the state notification method according to the present embodiment, such as data indicating a first threshold value (described later) and data indicating a second threshold value (described later), and various applications, for example. Herein, examples of the recording medium (not illustrated) include a magnetic recording medium such as a hard disk, non-volatile memory such as flash memory, and the like. Additionally, the recording medium (not illustrated) may also be removable from the medical observation apparatus 100.

The communication device (not illustrated) is a communication device provided in the medical observation apparatus 100, and fulfills a role of communicating in a wireless or wired manner with an external apparatus such as the display apparatus 200. Herein, examples of the communication device (not illustrated) include an IEEE 802.15.1 port and transmitting-receiving circuit (wireless communication), an IEEE 802.11 port and transmitting-receiving circuit (wireless communication), a communication antenna and a radio frequency (RF) circuit (wireless communication), a local area network (LAN) terminal and a transmitting-receiving circuit (wired communication), and the like.

[1-2-1] Base 102

The base 102 is the base of the medical observation apparatus 100. One end of the arm 104 is connected to the base 102, and the base 102 supports the arm 104 and the imaging device 106.

Also, casters are provided on the base 102, for example, and the medical observation apparatus 100 contacts the floor through the casters. By providing the casters, the medical observation apparatus 100 is able to move easily over the floor by the casters.

[1-2-2] Arm 104

The arm 104 includes multiple links joined to each other by joint sections.

In addition, the arm 104 supports the imaging device 106. The imaging device 106 supported by the arm 104 is movable three-dimensionally, and after moving, the position and the attitude of the imaging device 106 are maintained by the arm 104.

More specifically, the arm 104 includes, for example, multiple joint sections 110a, 110b, 110c, 110d, 110e, and 110f, and multiple links 112a, 112b, 112c, 112d, 112e, and 112f rotatably joined to each other by the joint sections 110a, 110b, 110c, 110d, 110e, and 110f. The rotatable range of each of the joint sections 110a, 110b, 110c, 110d, 110e, and 110f is set arbitrarily during the design stage, the manufacturing stage, or the like so that the desired motion of the arm 104 is realized.

In other words, in the medical observation apparatus 100 illustrated in FIG. 1, six degrees of freedom are realized in relation to the movement of the imaging device 106 by six rotation axes (first axis O1, second axis O2, third axis O3, fourth axis O4, fifth axis O5, and sixth axis O6) corresponding to the six joint sections 110a, 110b, 110c, 110d, 110e, and 110f included in the arm 104. More specifically, in the medical observation apparatus 100 illustrated in FIG. 1, motion with six degrees of freedom, including three degrees of translational freedom and three degrees of rotational freedom, is realized.

Actuators (not illustrated) are provided in each of the joint sections 110a, 110b, 110c, 110d, 110e, and 110f. Each of the joint sections 110a, 110b, 110c, 110d, 110e, and 110f rotates about the corresponding rotation axis by the driving of the actuators (not illustrated). The driving of the actuators (not illustrated) is controlled by, for example, a processor that functions as the control section described later, or an external control apparatus (not illustrated).

By having each of the joint sections 110a, 110b, 110c, 110d, 110e, 110f rotate about the corresponding rotation axis by the driving of the actuators (not illustrated), various operations of the arm 104, such as extending and contracting (folding up) the arm 104, for example, are realized.

The joint section 110a has an approximately cylindrical shape, and supports the imaging device 106 (the top end of the imaging device 106 in FIG. 1) on the front end portion of the joint section 110a (the bottom end portion in FIG. 1), so as to allow revolution about a rotation axis (first axis O1) parallel to the central axis of the imaging device 106. Herein, the medical observation apparatus 100 is configured so that the first axis O1 is aligned with the optical axis in the imaging device 106. In other words, by causing the imaging device 106 to revolve about the first axis O1 illustrated in FIG. 1, the medical captured image captured by the imaging device 106 becomes an image which has changed so that the field of view rotates.

The link 112a is an approximately rod-shaped member, and securely supports the joint section 110a. The link 112a extends in a direction orthogonal to the first axis O1, for example, and is connected to the joint section 110b.

The joint section 110b has an approximately cylindrical shape, and supports the link 112a so as to allow revolution about a rotation axis (second axis O2) orthogonal to the first axis O1. Also, the link 112b is securely connected to the joint section 110b.

The link 112b is an approximately rod-shaped member, and extends in a direction orthogonal to the second axis O2. Also, each of the joint section 110b and the joint section 110c is connected to the link 112b.

The joint section 110c has an approximately cylindrical shape, and supports the link 112b so as to allow revolution about a rotation axis (third axis O3) mutually orthogonal to each of the first axis O1 and the second axis O2. Also, one end of the link 112c is securely connected to the joint section 110c.

Herein, by having the front end side (the side on which the imaging device 106 is provided) of the arm 104 revolve about the second axis O2 and the third axis O3, the imaging device 106 can be made to move so that the position of the imaging device 106 in the horizontal plane is changed. In other words, in the medical observation apparatus 100, controlling the rotation about the second axis O2 and the third axis O3 makes it possible to move the field of view of the medical captured image in a flat plane.

The link 112c is a member in which one end has an approximately cylindrical shape, and the other end has an approximately rod-like shape. On the side of the one end of the link 112c, the joint section 110c is securely connected so that the central axis of the joint section 110c and the central axis of the approximately cylindrical shape are the same. Also, on the side of the other end of the link 112c, the joint section 110d is connected.

The joint section 110d has an approximately cylindrical shape, and supports the link 112c so as to allow revolution about a rotation axis (fourth axis O4) orthogonal to the third axis O3. The link 112d is securely connected to the joint section 110d.

The link 112d is an approximately rod-shaped member, and extends orthogonally to the fourth axis O4. One end of the link 112d is securely connected to the joint section 110d so as to abut the approximately cylindrical side face of the joint section 110d. Also, the joint section 110e is connected to the other end of the link 112d (the end on the opposite side of the side where the joint section 110d is connected).

The joint section 110e has an approximately cylindrical shape, and supports one end of the link 112d so as to allow revolution about a rotation axis (fifth axis O5) parallel to the fourth axis O4. Also, one end of the link 112e is securely connected to the joint section 110e.

Herein, the fourth axis O4 and the fifth axis O5 are rotation axis about which the imaging device 106 may be moved in the vertical direction. By having the front end side (the side on which the imaging device 106 is provided) of the arm 104 revolve about the fourth axis O4 and the fifth axis O5, the position of the imaging device 106 in the vertical direction changes. Thus, by having the front end side (the side on which the imaging device 106 is provided) of the arm 104 revolve about the fourth axis O4 and the fifth axis O5, changing the distance between the imaging device 106 and an observation target, such as an operating site of a patient, becomes possible.

The link 112e is a member that includes a combination of a first member having an approximate L-shape with one edge extending in the vertical direction while the other edge extends in the horizontal direction, and a rod-like second member that extends vertically downward from the part of the first member that extends in the horizontal direction. The joint section 110e is securely connected to the part of the first member of the link 112e that extends in the vertical direction. Also, the joint section 110f is connected to the second member of the link 112e.

The joint section 110f has an approximately cylindrical shape, and supports the link 112e so as to allow revolution about a rotation axis (sixth axis O6) parallel to the vertical direction. Also, the link 112f is securely connected to the joint section 110f.

The link 112f is an approximately rod-shaped member, and extends in the vertical direction. The joint section 110f is connected to one end of the link 112f. Also, the other end of the link 112f (the end on the opposite side of the side where the joint section 110f is connected) is securely connected to the base 102.

By having the arm 104 include the configuration indicated above, in the medical observation apparatus 100, six degrees of freedom are realized with respect to the movement of the imaging device 106.

Note that the configuration of the arm 104 is not limited to the example indicated above.

For example, each of the joint sections 110a, 110b, 110c, 110d, 110e, and 110f of the arm 104 may be provided with a brake that restrains rotation in each of the joint sections 110a, 110b, 110c, 110d, 110e, and 110f. The brake according to the present embodiment may be a brake of an arbitrary method, such as a mechanically driven brake or an electrically driven electromagnetic brake, for example.

The driving of the above brakes is controlled by, for example, a processor that functions as the control section described later, or an external control apparatus (not illustrated). By controlling the driving of the above brakes, in the medical observation apparatus 100, the operating mode of the arm 104 is set. Examples of operating modes of the arm 104 include a locked mode and a free mode.

Herein, the locked mode according to the present embodiment is, for example, an operating mode in which the position and the attitude of the imaging device 106 are locked by using brakes to restrain rotation about each rotation axis provided in the arm 104. By having the arm 104 enter the locked mode, the operating state of the medical observation apparatus 100 becomes a locked state in which the position and the attitude of the imaging device 106 are locked.

Also, the free mode according to the present embodiment is an operating mode in which the above brakes are released, thereby allowing each rotation axis provided in the arm 104 to rotate freely. For example, in the free mode, the position and the attitude of the imaging device 106 are adjustable by direct operations performed by the surgeon. Herein, a direct operation according to the present embodiment means, for example, an operation in which the surgeon grips the imaging device 106 with his or her hand, and directly moves the imaging device 106.

[1-2-3] Imaging Device 106

The imaging device 106 is supported by the arm 104, and images an observation target such as an operating site of a patient, for example. Imaging in the imaging device 106 is controlled by, for example, a processor that functions as the control section described later, or an external control apparatus (not illustrated).

The imaging device 106 has a configuration corresponding to an electronic imaging microscope, for example.

Figure 3:
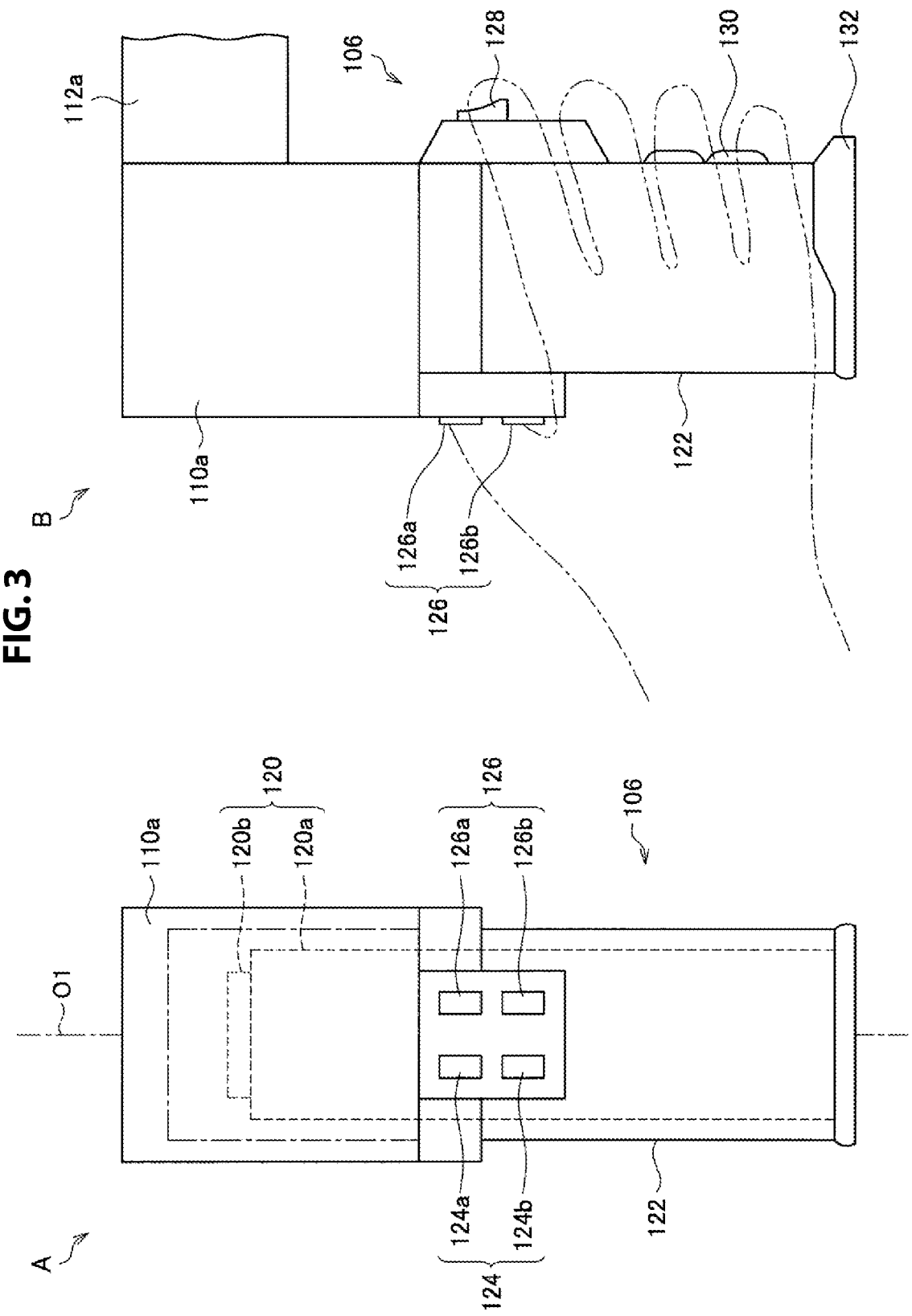
FIG. 3 is an explanatory diagram for explaining an example of the configuration of an imaging device provided in a medical observation apparatus according to the present embodiment.

FIG. 3 is an explanatory diagram for explaining an example of the configuration of the imaging device 106 provided in the medical observation apparatus 100 according to the present embodiment.

For example, the imaging device 106 includes an imaging member 120 and a barrel member 122 having an approximately cylindrical shape, with the imaging member 120 being provided inside the barrel member 122.

On an aperture on the bottom end of the barrel member 122 (the lower end in FIG. 3), for example, a cover glass (not illustrated) for protecting the imaging member 120 is provided.

Additionally, for example, a light source (not illustrated) is provided inside the barrel unit 122, and during imaging, the subject is irradiated with illuminating light radiating from the light source through the cover glass. Reflected light (observation light) from the subject irradiated with illuminating light enters the imaging member 120 through the cover glass (not illustrated), whereby an image signal indicating the subject (an image signal indicating a taken image) is obtained by the imaging member 120.

As the imaging member 120, any of various known types of configurations used in an electronic imaging microscope section can be applied.

To give one example, the imaging member 120 includes an optical system 120*a* and an image sensor 120*b* including an imaging element that takes an image of an observation target with light transmitted through the optical system 120*a*, for example. The optical system 120*a* includes optical elements such as a mirror and one or multiple lenses, such as an objective lens, a zoom lens, and a focus lens, for example. Examples of the image sensor 120*b* include an image sensor using multiple imaging elements, such as a complementary metal-oxide semiconductor (CMOS) or a charge-coupled device (CCD).

The imaging member 120 may also include a pair of imaging elements, or in other words, be configured to function as what is called a stereo camera. The imaging member 120 is equipped with one or multiple functions typically provided in an electronic imaging microscope section, including at least a zoom function (one or both of an optical zoom function and an electronic zoom function), such as an autofocus (AF) function.

In addition, the imaging member 120 may also be configured to be capable of imaging at what are called high resolutions, such as 4K and 8K, for example. By configuring the imaging member 120 to be capable of imaging at high resolutions, it becomes possible to ensure a predetermined resolution (such as full HD image quality, for example), while also displaying an image on the display apparatus 200 having a large display screen, such as 50 inches or more, for example. For this reason, visibility is improved for the surgeon watching the display screen. Also, by configuring the imaging member 120 to be capable of imaging at high resolutions, even if the taken image is enlarged by the electronic zoom function and displayed on the display screen of the display apparatus 200, it is still possible to ensure a predetermined resolution. Furthermore, in the case of using the electronic zoom function to ensure a predetermined resolution, since it is possible to reduce the performance of the optical zoom function in the imaging device 106, the optical system of the imaging device 106 can be simplified, and the imaging device 106 can be configured more compactly.

In the imaging device 106, for example, various operating devices for controlling the operation of the imaging device 106 are provided. For example, in FIG. 3, a zoom switch 124, a focus switch 126, and an operating mode change switch 128 are provided on the imaging device 106. Note that the positions and shapes in which to provide the zoom switch 124, the focus switch 126, and the operating mode change switch 128 obviously are not limited to the example illustrated in FIG. 3.

The zoom switch 124 and the focus switch 126 are an example of an operating device for adjusting the imaging parameters in the imaging device 106.

The zoom switch 124 includes, for example, a zoom-in switch 124*a* that increases the zoom magnification (enlargement ratio), and a zoom-out switch 124*b* that decreases the zoom magnification. By performing an operation on the zoom switch 124, the zoom magnification is adjusted, and the zoom is adjusted.

The focus switch 126 includes, for example, a long-range focus switch 126*a* that increases the focal length to the observation target (subject), and a close-range focus switch 126*b* that decreases the focal length to the observation target. By performing an operation on the focus switch 126, the focal length is adjusted, and the focus is adjusted.

The operating mode change switch 128 is an example of an operating device for changing the operating mode of the arm 104 in the imaging device 106. By performing an operation on the operating mode change switch 128, the operating mode of the arm 104 is changed. Examples of operating modes of the arm 104 include a locked mode and a free mode, as described above.

One example of an operation with respect to the operating mode change switch 128 is an operation of pressing the operating mode change switch 128. For example, the operating mode of the arm 104 becomes the free mode while the surgeon is pressing the operating mode change switch 128, and the operating mode of the arm 104 becomes the locked mode when the surgeon is not pressing the operating mode change switch 128.

In addition, the imaging device 106 is provided with, for example, an anti-slip member 130 and a projecting member 132 in order to further raise operability, convenience, and the like when an operator who performs operations on various operation devices performs an operation.

The anti-slip member 130 is a member provided to prevent slipping of an operating body such as a hand when, for example, the operator performs an operation on the barrel member 122 with the operating body. The anti-slip member 130 is formed with a material having a large coefficient of friction, for example, and has a slip-resistant structure due to unevenness or the like.

The projecting member 132 is member provided to prevent an operating body such as a hand blocking the field of view of the optical system 120*a* when the operator performs an operation on the barrel member 122 with the operating body, or to prevent a cover glass (not illustrated) from becoming dirty due to the cover glass being contacted by the operating body when an operation is performed with the operating body.

Note that the position and shape in which each of the anti-slip member 130 and the projecting member 132 is provided obviously are not limited to the example illustrated in FIG. 3. In addition, the imaging device 106 does not have to be provided with one or both of the anti-slip member 130 and the projecting member 132.

The image signal (image data) generated by imaging in the imaging device 106 is subjected to image processing in a processor that functions as the control section described later, for example. Examples of image processing according to the present embodiment include one or multiple processes from among various processes such as gamma correction, white balance adjustment, image enlargement or reduction related to the electronic zoom function, and pixel interpolation, for example. Note that in the case in which the medical observation system according to the present embodiment includes a control apparatus (not illustrated) that controls various operations in the medical observation apparatus 100, the image processing according to the present embodiment may also be performed in the control apparatus (not illustrated).

For example, the medical observation apparatus 100 transmits a display control signal and the image signal subjected to imaging processing as above to the display apparatus 200.

By transmitting the display control signal and the image signal to the display apparatus 200, on the display screen of the display apparatus 200, a medical captured image in which the observation target is imaged (for example, a taken image in which the operating site is imaged) is displayed enlarged or reduced at a desired magnification by one or both of the optical zoom function and the electronic zoom function.

[1-2-4] Sensors (Sensor Group)

The sensors (sensor group) are devices for sensing which are provided in the medical observation apparatus 100.

The sensors according to the present embodiment may be distance sensors capable of measuring the distance to an object by an arbitrary method, such as the time of flight (TOF) method.

One or multiple distance sensors are provided in the part corresponding to the sterile region in the medical observation apparatus 100, and measure the distance to an object existing in the periphery of the part corresponding to the sterile region. For example, the one or multiple distance sensors are arranged to measure the distance to objects existing all around the part corresponding to the sterile region. Note that the sensing range of the one or multiple distance sensors may be set arbitrarily in the design stage, the manufacturing stage, or the like, for example.

Herein, the part corresponding to the sterile region in the medical observation apparatus 100 may be "a part including the imaging device 106 and at least a portion of the arm 104". "A part including the imaging device 106 and at least a portion of the arm 104" refers to, for example, "the imaging device 106, and the entirety of the arm 104", or "the imaging device 106, and a portion of the arm 104". "The imaging device 106, and a portion of the arm 104" may be, for example, "the imaging device 106, and the part of the arm 104 up to the links 112*a* and 112*b*", "the imaging device 106, and the part of the arm 104 up to the links 112*a*, 112*b*, and 112*c*", or the like.

Note that the part corresponding to the sterile region in the medical observation apparatus 100 is not limited to the examples indicated above. For example, the part corresponding to the sterile region in the medical observation apparatus 100 may also be the entire medical observation apparatus 100.

As described above, in the medical observation apparatus 100, the part covered by the medical sterile cover becomes the sterile region, for example. The part covered by the medical sterile cover is appropriate as the part corresponding to the sterile region in the medical observation apparatus 100. In other words, the above "part including the imaging device 106 and at least a portion of the 104" may change depending on the range over which the medical sterile cover covers the medical observation apparatus 100.

In addition, as described above, the medical observation apparatus according to the present embodiment may also be an optical medical observation apparatus. In the case in which the medical observation apparatus according to the present embodiment is an optical medical observation apparatus, at least the part covered by the medical sterile cover in the optical medical observation apparatus becomes the part corresponding to the sterile region in the optical medical observation apparatus. Additionally, in the case in which medical observation apparatus according to the present embodiment is an optical medical observation apparatus, the sensors (sensor group) according to the present embodiment, including distance sensors, are provided to measure the distance to an object existing in the periphery of the part covered by the medical sterile cover above.

Note that the sensors according to the present embodiment are not limited to distance sensors.

For example, the medical observation apparatus 100 may also have contact sensors capable of detecting contact directly by an arbitrary method, such as strain gauges. Additionally, the contact sensors according to the present embodiment may also be motion sensors such as acceleration sensors, for example. In the case in which a motion sensor functions as a contact sensor, contact is estimated according to detected motion.

For example, one or multiple contact sensors are provided in the part corresponding to the sterile region in the medical observation apparatus 100, and detect the contact of an object with respect to the part corresponding to the sterile region. Note that the contact sensors are not limited to being provided in the part corresponding to the sterile region in the medical observation apparatus 100, and may also be provided at arbitrary positions on the medical observation apparatus 100 enabling the detection of the contact of an object with respect to the part corresponding to the sterile region.

Figure 4:
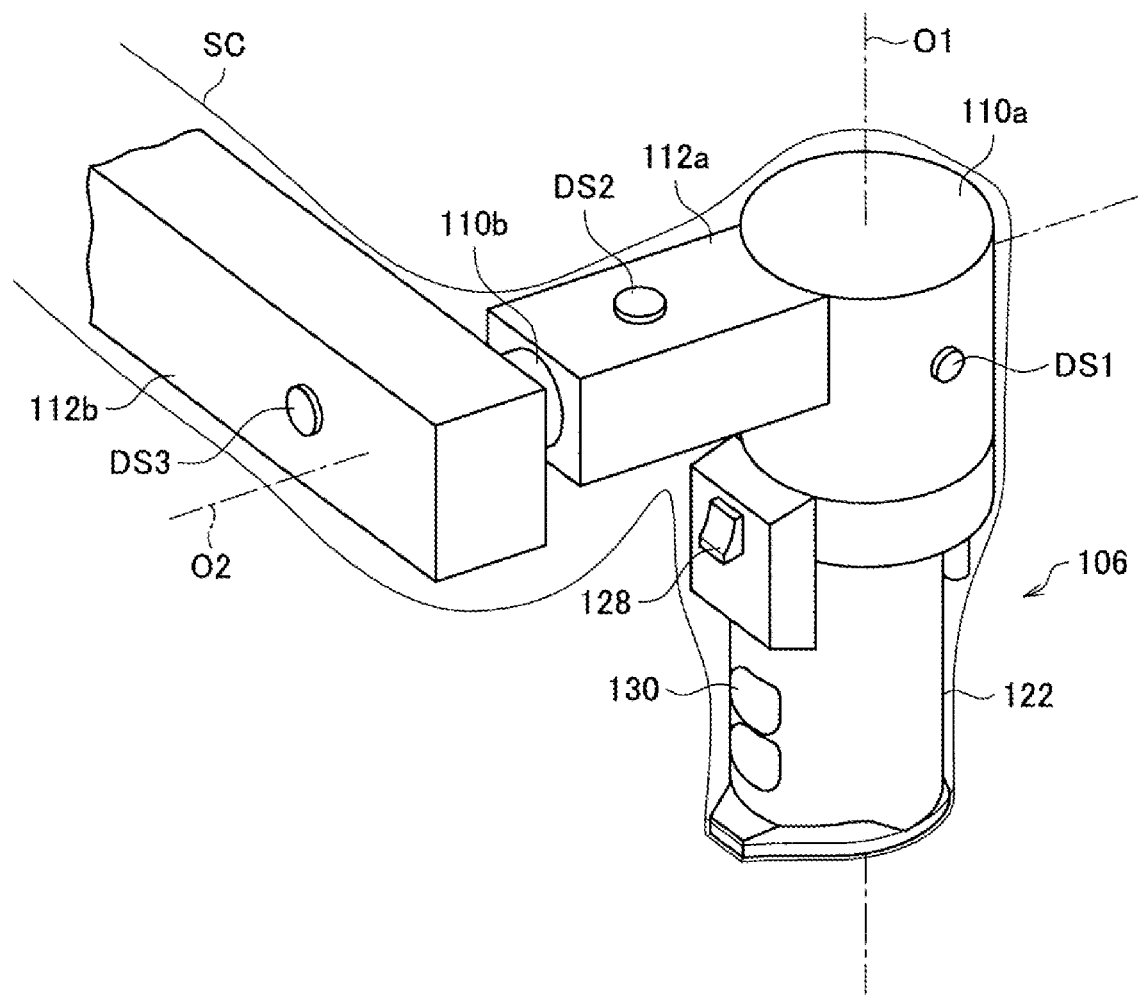
FIG. 4 is an explanatory diagram illustrating an example of sensors (a sensor group) provided in the medical observation apparatus according to the present embodiment.

FIG. 4 is an explanatory diagram illustrating an example of the sensors (sensor group) provided in the medical observation apparatus 100 according to the present embodiment, and illustrates an example in which distance sensors are provided on the medical observation apparatus 100. FIG. 4 illustrates the part covered by the medical sterile cover SC in the medical observation apparatus 100, that is, the part corresponding to the sterile region in the medical observation apparatus 100.

In the part corresponding to the sterile region in the medical observation apparatus 100 illustrated in FIG. 4, multiple distance sensors designated the distance sensors DS1, DS2, DS3, and so on are provided. Each distance sensor is connected, in a wired or wireless manner, to a processor that functions as a control section described later. The processor performs a process related to the state notification method according to the present embodiment, on the basis of detection results acquired from each of the distance sensors.

Note that the positions of the distance sensors provided in the part corresponding to the sterile region in the medical observation apparatus 100, as well as the number of distance sensors, obviously are not limited to the example illustrated in FIG. 4.

Figure 5:
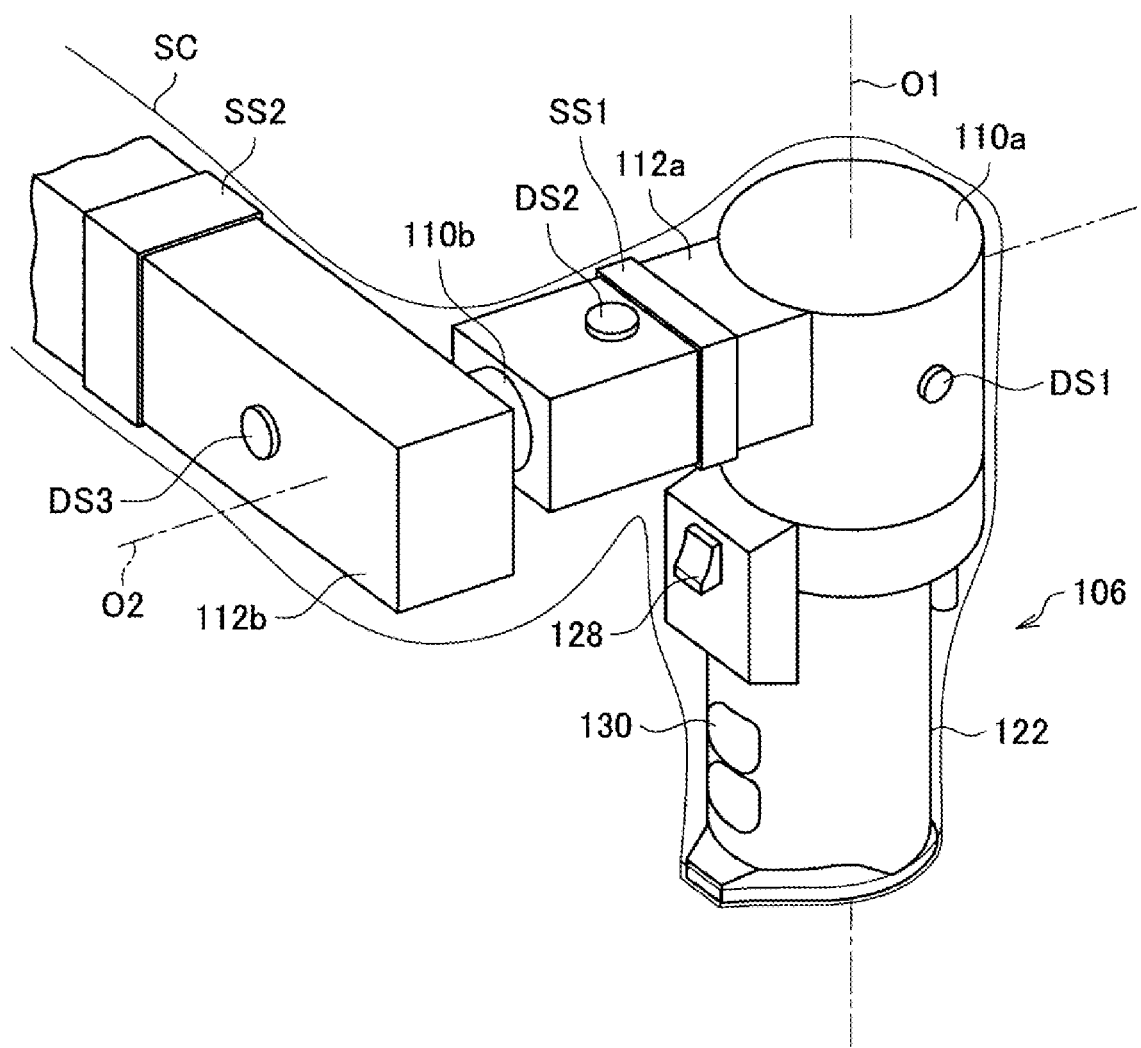
FIG. 5 is an explanatory diagram illustrating another example of sensors (a sensor group) provided in the medical observation apparatus according to the present embodiment.

FIG. 5 is an explanatory diagram illustrating another example of the sensors (sensor group) provided in the medical observation apparatus 100 according to the present embodiment, and illustrates an example in which distance sensors and strain gauges (one example of contact sensors; the same applies similarly hereinafter) are provided on the medical observation apparatus 100. Similarly to FIG. 4, FIG. 5 illustrates the part covered by the medical sterile cover SC in the medical observation apparatus 100, that is, the part corresponding to the sterile region in the medical observation apparatus 100.

In the part corresponding to the sterile region in the medical observation apparatus 100 illustrated in FIG. 5, similarly to the example illustrated in FIG. 4, multiple distance sensors designated the distance sensors DS1, DS2, DS3, and so on are provided. Similarly to the example illustrated in FIG. 4, each distance sensor is connected, in a wired or wireless manner, to a processor that functions as the control section described later.

Also, in the part corresponding to the sterile region in the medical observation apparatus 100 illustrated in FIG. 5, multiple strain gauges designated the strain gauges SS1, SS2, SS3, and so on are provided. Each strain gauge is connected, in a wired or wireless manner, to a processor that functions as the control section described later. The processor performs a process related to the state notification method according to the present embodiment, on the basis of detection results acquired from each of the strain gauges.

Note that the positions of the distance sensors provided in the part corresponding to the sterile region in the medical observation apparatus 100, as well as the number of distance sensors, obviously are not limited to the example illustrated in FIG. 5. Also, the positions of the strain gauges provided in the part corresponding to the sterile region in the medical observation apparatus 100, as well as the number of strain gauges, obviously are not limited to the example illustrated in FIG. 5. Furthermore, as described above, the contact sensors provided in the part corresponding to the sterile region in the medical observation apparatus 100 are not limited to strain gauges.

The medical observation apparatus 100 includes the hardware configuration illustrated with reference to FIGS. 1, 3 to 5, for example.

Note that the hardware configuration of the medical observation apparatus according to the present embodiment is not limited to the configuration illustrated with reference to FIGS. 1, 3 to 5.

For example, the medical observation apparatus according to the present embodiment may also be a configuration not provided with the base 102, in which the arm 104 is directly attached to the ceiling, a wall, or the like of the operating room or the like. For example, in the case in which the arm 104 is attached to the ceiling, the medical observation apparatus according to the present embodiment becomes a configuration in which the arm 104 hangs down from the ceiling.

Also, although FIG. 1 illustrates an example configured so that six degrees of freedom are realized with respect to the driving of the imaging device 106, the configuration of the arm 104 is not limited to a configuration whereby the degrees of freedom with respect to the driving of the imaging device 106 become six degrees of freedom. For example, it is sufficient to configure the arm 104 so that the imaging device 106 can move appropriately in accordance with the application, and factors such as the number and arrangement of joint sections and links, and the directions of the drive shafts of the joint sections can be set appropriately so that the arm 104 has the desired degrees of freedom.

Also, although FIGS. 1 and 3 illustrate an example in which various types of operating devices for controlling the operation of the imaging device 106 are provided on the imaging device 106, some or all of the operating devices illustrated in FIGS. 1 and 3 may also not be provided on the imaging device 106. To give one example, the various types of operating devices for controlling the operation of the imaging device 106 may also be provided in another part other than the imaging device 106 included in the medical observation apparatus according to the present embodiment. Also, to give another example, the various types of operating devices for controlling the operation of the imaging device 106 may also be external operating devices, such as a footswitch or a remote controller.

Also, the sensors (sensor group), such as the distance sensors and the strain gauges illustrated in FIGS. 4 and 5, may also be sensors (a sensor group) separate from the medical observation apparatus according to the present embodiment.

Figure 6:
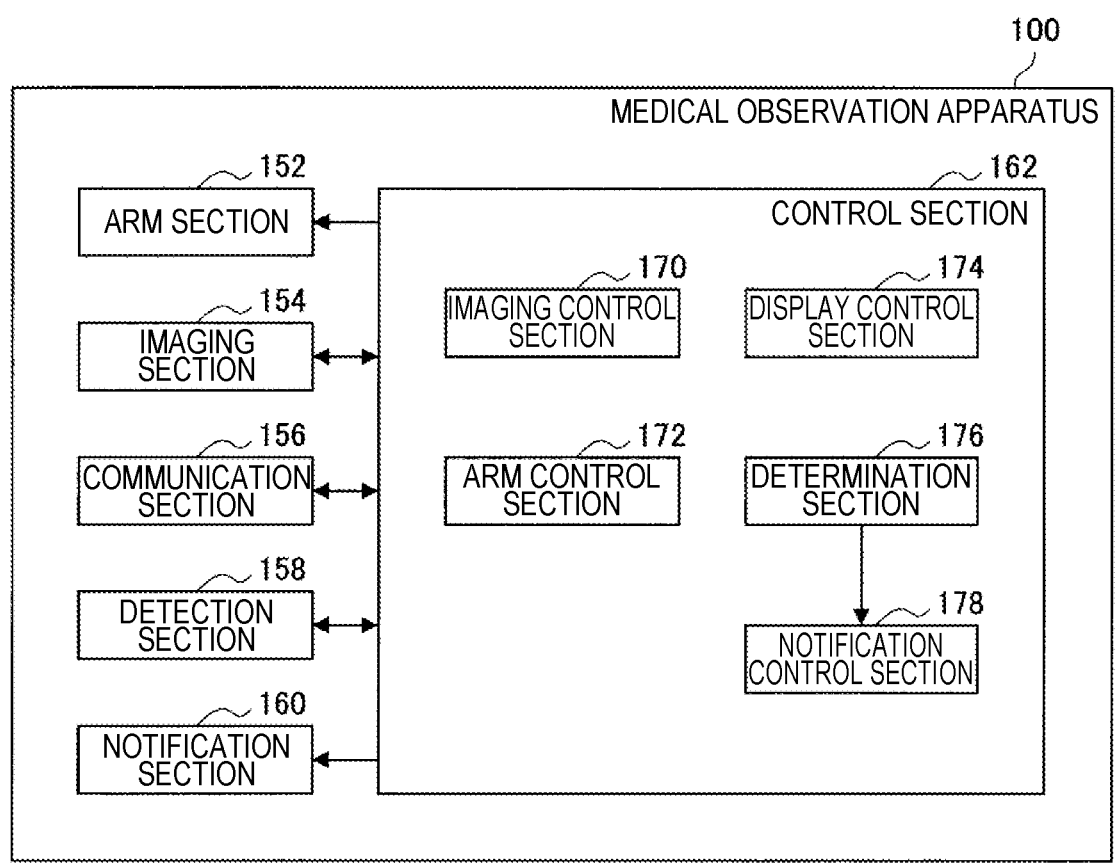
FIG. 6 is a function block diagram illustrating an example of a configuration of a medical observation apparatus according to the present embodiment.

Next, the medical observation apparatus 100 illustrated in FIG. 1 will be described using function blocks. FIG. 6 is a function block diagram illustrating an example of the configuration of the medical observation apparatus 100 according to the present embodiment.

For example, the medical observation apparatus 100 is provided with an arm section 152, an imaging section 154, a communication section 156, a detection section 158, a notification section 160, and a control section 162.

The arm section 152 includes the arm 104, and supports the imaging device 106 included in the imaging section 154.

The imaging section 154 includes the imaging device 106, and images an observation target. Imaging in the imaging section 154 is controlled by the control section 162, for example.

The communication section 156 is a communication device provided in the medical observation apparatus 100, and fulfills a role of communicating in a wireless or wired manner with an external apparatus such as the display apparatus 200. The communication section 156 includes the communication device (not illustrated) described above, for example. Communication in the communication section 156 is controlled by the control section 162, for example.

The detection section 158 is a detector provided in the medical observation apparatus 100, and acquires detection values related to the process related to the state notification method according to the present embodiment.

The detection section 158 includes one or multiple distance sensors, for example. The distance sensors included in the detection section 158 acquire detection values indicating "the distance between the part corresponding to the sterile region and an object existing in the periphery of the part corresponding to the sterile region".

Also, the detection section 158 additionally may include one or multiple contact sensors, for example. The contact sensors included in the detection section 158 acquire detection values which are produced in response to contact, such as a voltage difference produced in response to strain (one example of a detection value in the case in which the contact sensors are strain gauges).

The notification section 160 is a notifier provided in the medical observation apparatus 100, and notifies external apparatus of notification content related to the state notification method according to the present embodiment. The notification section 160 includes a notification device that issues the notification of the notification content.

The notification content related to the state notification method according to the present embodiment may be, for example, one or both of "a state in which an object is approaching the part corresponding to the sterile region" and "a state in which an object has made contact with the part corresponding to the sterile region". Hereinafter, the state in which an object is approaching the part corresponding to the sterile region is designated the "approaching state". Also, hereinafter, the state in which an object has made contact with the part corresponding to the sterile region is designated the "contacting state".

For example, the notification section 160 issues the notification of the notification content by a visual notification, an aural notification, or a combination of the two.

For example, the notification section 160 includes one or multiple indicator lamps (one example of a notification device), and issues a visual notification of the notification content by turning on the indicator lamps corresponding to the notification content. By having the indicator lamps corresponding to the notification content turn on, a medical personnel member such as the surgeon is able to visually recognize the notification content.

Examples of the position where the indicator lamps are provided include, for example, a part of arm 104, a part of the imaging device 106, or the like. In the case in which the indicator lamps are provided on a part of the arm 104, the position where the indicator lamps are provided may be the part corresponding to the sterile region, or a part other than the part corresponding to the sterile region. Note that the position where the indicator lamps are provided obviously is not limited to the examples given above.

Note that the device that issues a visual notification of the notification content included in the notification section 160 is not limited to indicator lamps, and may also be a display device (one example of a notification device) capable of displaying text and images (such as icons, for example) corresponding to the notification content. Similarly to the position where the indicator lamps are provided, for example, the position where the display device is provided may be a part of the arm 104, a part of the imaging device 106, or the like.

Additionally, for example, the notification section 160 includes an audio output device such as a speaker (one example of a notification device), and issues an aural notification of the notification content by outputting audio (including music) corresponding to the notification content from the audio output device. By having audio corresponding to the notification content be output from the audio output device, a medical personnel member such as the surgeon is able to aurally recognize the notification content.

The audio output device may be provided at an arbitrary position in the medical observation apparatus 100, for example.

Notifications in the notification section 160 are controlled by the control section 162 (more specifically, a notification control section described later).

Note that notifications in the notification section 160 are not limited to the examples given above. For example, the notification section 160 is able to issue a notification of the notification content by an arbitrary method which is perceivable by a medical personnel member such as the surgeon.

The control section 162 includes the processor (not illustrated) described above, for example, and fulfills a role of controlling the medical observation apparatus 100 overall. In addition, the control section 162 fulfills a role of leading the execution of the processes related to the state notification method described later. Note that the processes according to the state notification method in the control section 162 may also be performed in a distributed manner by multiple processing circuits (such as multiple processors, for example).

More specifically, the control section 162 includes an imaging control section 170, an arm control section 172, a display control section 174, a determination section 176, and a notification control section 178, for example.

The imaging control section 170 controls the imaging device 106 included in the imaging section 154. Examples of the control of the imaging device 106 include control of one or multiple functions typically provided in an electronic imaging microscope section, including control of at least a zoom function (one or both of an optical zoom function and an electronic zoom function), such as control of an AF function.

The arm control section 172 controls the driving of the arm 104 included in the arm section 152. One example of control of the driving of the arm 104 includes, for example, "applying a control signal that controls driving to the actuators (not illustrated) corresponding to each of the joint sections 110a, 110b, 110c, 110d, 110e, and 110f", and the like.

For example, the display control section 174 controls the display on the display apparatus 200 by conveying the display control signal and the image signal to the communication device (not illustrated) included in the communication section 156, and causing the display control signal and the image signal to be transmitted to the display apparatus 200. Note that the control of communication in the communication section 156 may also be performed by a communication control section (not illustrated) included in the control section 162.

Additionally, the display control section 174 may also function as the notification control section 178 described later. In the case of functioning as the notification control section 178, the display control section 174 controls the display on the display apparatus 200 in conjunction with the determination section 176 described later, and causes text, images, or a combination of the two corresponding to the notification content to be displayed on the display screen of the display apparatus 200. In other words, in the case of functioning as the notification control section 178, the display control section 174 fulfills a role of issuing a visual notification of the notification content (for example, one or both of the approaching state and the contacting state).

The determination section 176 fulfills a role of performing a state determination process (described later) in the process related to the state notification method according to the present embodiment, and determines a "state related to the relationship between the part corresponding to the sterile region and an object".

An example of the "state related to the relationship between the part corresponding to the sterile region and an object" determined by the determination section 176 is the approaching state. In addition, the determination section 176 additionally may determine the contacting state as the "state related to the relationship between the part corresponding to the sterile region and an object".

The determination result in the determination section 176 is transmitted to the notification control section 178, and in the notification control section 178, a process corresponding to the determination result is performed. Also, in the case in which the display control section 174 functions as the notification control section 178, the determination result in the determination section 176 is transmitted to the display control section 174, and in the display control section 174, the display in the display apparatus 200 is controlled on the basis of the determination result.

The notification control section 178 fulfills a role of performing a notification control process (described later) in the process related to the state notification method according to the present embodiment, and on the basis of the determination result in the determination section 176, causes a notification of the notification content corresponding to the determination result to be issued.

In the case in which the approaching state is determined in the determination section 176, the notification control section 178 causes a notification of the approaching state to be issued, as indicated in (a) below. Also, in the case in which the approaching state and the contacting state are determined in the determination section 176, the notification control section 178 causes a notification of the approaching state to be issued as indicated in (a) below, and causes a notification of the contacting state to be issued as indicated in (b) below.

(a) Example of Process by Notification Control Section 178 in Case in which Approaching State is Determined in Determination Section 176

In the case in which the approaching state is determined in the determination section 176, the notification control section 178 causes a notification of the approaching state to be issued, on the basis of the determination result of the approaching state.

For example, the notification control section 178 causes the notification section 160 to issue a notification of the approaching state by controlling the notification device included in the notification section 160.

To give one example, the notification control section 178 transmits a signal for turning on an indicator lamp to an "indicator lamp that indicates the approaching state by turning on" (one example of a notification device) included in the notification section 160, and thereby causes the indicator lamp to turn on and issue a visual notification of the approaching state. To give another example, the notification control section 178 transmits an audio signal expressing "audio indicating the approaching state" to the audio output device (one example of a notification device) included in the notification section 160, and thereby causes the audio output device to output the "audio indicating the approaching state" and issue an aural notification of the approaching state. Furthermore, the notification control section 178 may cause the above indicator lamp to turn and also cause the above audio output device to output audio, and thereby cause a notification of the approaching state to be issued visually and aurally.

In addition, by having the notification control section 178 control an external notification device, such as an external display device like the display apparatus 200, or an external audio output device, for example, it is also possible to cause an external notification device to issue a notification of the approaching state. In the case of causing an external display device such as the display apparatus 200 to issue a notification of the approaching state, the display control section 174 may also fulfill the role of the notification control section 178.

To give one example, the notification control section 178 causes a display control signal and an image signal expressing "text, images, or the like indicating the approaching state" to an external display device, and thereby causes the notification content corresponding to the image signal to be displayed on the display screen of the external display device, and causes a visual notification of the approaching state to be issued. To give another example, the notification control section 178 transmits an audio signal expressing "audio indicating the approaching state" to an external audio output device, and thereby causes the external audio output device to output the "audio indicating the approaching state", and causes an aural notification of the approaching state to be issued. Furthermore, the notification control section 178 may cause a visual and aural notification of the approaching state to be issued by causing information to be displayed on the display screen of the above external display device and by causing audio to be output from the above external audio output device.

In other words, for example, the notification control section 178 issues a notification of the approaching state by one or both of a visual method and an aural method. Note that it is also possible for the notification control section 178 to issue a notification of the approaching state by an arbitrary notification method which is perceivable by a medical personnel member, such as by inducing vibration in a vibration device (one example of an external notification device) worn by a medical personnel member such as the surgeon.

(b) Example of Process by Notification Control Section 178 in Case in which Approaching State and Contacting State are Determined in Determination Section 176

In the case in which the approaching state is determined in the determination section 176, as indicated in (a) above, the notification control section 178 causes a notification of the approaching state to be issued, on the basis of the determination result of the approaching state. Also, in the case in which the contacting state additionally is determined in the determination section 176, the notification control section 178 additionally causes a notification of the contacting state to be issued, on the basis of the determination result of the contacting state.

For example, the notification control section 178 causes the notification section 160 to issue a notification of the contacting state by controlling the notification device included in the notification section 160.

To give one example, the notification control section 178 transmits a signal for turning on an indicator lamp to an "indicator lamp that indicates the contacting state by turning on" (one example of a notification device) included in the notification section 160, and thereby causes the indicator lamp to turn on and issue a visual notification of the contacting state. To give another example, the notification control section 178 transmits an audio signal expressing "audio indicating the contacting state" to the audio output device (one example of a notification device) included in the notification section 160, and thereby causes the audio output device to output the "audio indicating the contacting state" and issue an aural notification of the contacting state. Furthermore, the notification control section 178 may cause the above indicator lamp to turn and also cause the above audio output device to output audio, and thereby cause a notification of the contacting state to be issued visually and aurally.

In addition, by having the notification control section 178 control an external notification device, such as an external display device like the display apparatus 200, or an external audio output device, for example, it is also possible to cause an external notification device to issue a notification of the contacting state. In the case of causing an external display device such as the display apparatus 200 to issue a notification of the contacting state, the display control section 174 may also fulfill the role of the notification control section 178.

To give one example, the notification control section 178 causes a display control signal and an image signal expressing "text, images, or the like indicating the contacting state" to an external display device, and thereby causes the notification content corresponding to the image signal to be displayed on the display screen of the external display device, and causes a visual notification of the contacting state to be issued. To give another example, the notification control section 178 transmits an audio signal expressing "audio indicating the contacting state" to an external audio output device, and thereby causes the external audio output device to output the "audio indicating the contacting state", and causes an aural notification of the contacting state to be issued. Furthermore, the notification control section 178 may cause a visual and aural notification of the contacting state to be issued by causing information to be displayed on the display screen of the above external display device and by causing audio to be output from the above external audio output device.

In other words, for example, the notification control section 178 issues a notification of the contacting state by one or both of a visual method and an aural method. Note that it is also possible for the notification control section 178 to issue a notification of the contacting state by an arbitrary notification method which is perceivable by a medical personnel member, such as by inducing vibration in a vibration device (one example of an external notification device) worn by a medical personnel member such as the surgeon.

For example, by including the determination section 176 and the notification control section 178 (or the display control section 174, the determination section 176, and the notification control section 178), the control section 162 fulfills a role of leading the execution of the processes related to the state notification method according to the present embodiment. Also, for example, by including the imaging control section 170, the arm control section 172, and the display control section 174, the control section 162 fulfills a role of controlling the medical observation apparatus 100 overall.

Note that the configuration of the control section 162 is not limited to the example illustrated in FIG. 6.

For example, the control section 162 can include an arbitrary configuration corresponding to how the functions included in the medical observation apparatus 100 are divided up, such as a configuration corresponding to how the processes related to the state notification method according to the present embodiment are divided up.

The medical observation apparatus 100 performs processes related to the state notification method according to the present embodiment described later with the configuration illustrated in FIG. 6, for example.

Note that the configuration of the medical observation apparatus according to the present embodiment is not limited to the configuration illustrated in FIG. 6.

For example, in the medical observation apparatus according to the present embodiment, one or more of the imaging control section 170, the arm control section 172, the display control section 174, the determination section 176, and the notification control section 178 illustrated in FIG. 6 can be provided separately from the control section 162 (for example, realized by a different processing circuit).

Additionally, in the medical observation apparatus according to the present embodiment, the configuration for realizing processes related to the state notification method according to the present embodiment is not limited to the configuration illustrated in FIG. 6. For example, the medical observation apparatus according to the present embodiment can take a configuration corresponding to how the processes related to the state notification method according to the present embodiment are divided up.

Also, in the case in which the medical observation apparatus according to the present embodiment is an optical medical observation apparatus, the medical observation apparatus according to the present embodiment may also not be provided with the imaging section 154.

Also, for example, in the case of communicating with an external apparatus via an external communication device having a function and configuration similar to the communication section 156, the medical observation apparatus according to the present embodiment may also not be provided with the communication section 156.

Additionally, for example, in the case in which the control section 162 performs the state determination process (described later) on the basis of detection results from external sensors (a sensor group) having functions and a configuration similar to the detection section 158, the medical observation apparatus according to the present embodiment may also not be provided with the detection section 158.

Also, in the case in which notifications are issued by an external notification device such as the display apparatus 200, the medical observation apparatus according to the present embodiment may also not be provided with the notification section 160.

Also, in the case in which the medical observation system according to the present embodiment includes the control apparatus (not illustrated), and the medical observation apparatus according to the present embodiment is controlled by the control apparatus (not illustrated), the medical observation apparatus according to the present embodiment may also not be provided with the control section 162.

Herein, the control apparatus (not illustrated) is, for example, provided with a control section having a function and configuration similar to the control section 162, and thereby performs processes related to the state notification method according to the present embodiment described later, and in addition, controls the operation in each structural element such as the arm section 152 and the imaging section 154 provided in the medical observation apparatus according to the present embodiment. The control apparatus (not illustrated) communicates with the medical observation apparatus according to the present embodiment via a provided communication device or a connected external communication device, and thereby controls the operation in each structural element provided in the medical observation apparatus according to the present embodiment.

Furthermore, in the case in which the medical observation system according to the present embodiment includes the control apparatus (not illustrated), and the medical observation apparatus according to the present embodiment is controlled by the control apparatus (not illustrated), it is also possible for the medical observation apparatus according to the present embodiment to take a configuration that does not include some of the functions of the control section 162.

[2] State Notification Method According to Present Embodiment

Next, processes related to the state notification method according to the present embodiment will be described. The following gives an example of a case in which the processes related to the state notification method according to the present embodiment are performed by the medical observation apparatus 100 (more specifically, the control section 162 included in the medical observation apparatus 100, for example). Note that, as described above, in the medical observation system according to the present embodiment, the processes related to the state notification method according to the present embodiment may also be performed by the control apparatus (not illustrated).

[2-1] Summary of State Notification Method According to Present Embodiment

As described above, if a site whose sterile state is not ensured, such as the face or head of a medical personnel member, comes into contact with the sterile region, the medical personnel member may need to re-cover the optical medical observation apparatus or electronic imaging medical observation apparatus with a new medical sterile cover. Also, as described above, the situation of re-covering with a new medical sterile cover may lead to reduced surgical efficiency, and in addition, increased costs due to the use of a new medical sterile cover are a concern.

Accordingly, the medical observation apparatus 100 determines the "state related to the relationship between the part corresponding to the sterile region and an object" (state determination process). Herein, the "state related to the relationship between the part corresponding to the sterile region and an object" determined by the medical observation apparatus 100 may be, as described above, the approaching state (a state in which an object is approaching the part corresponding to the sterile region). Also, as described above, the medical observation apparatus 100 may also determine the contacting state (a state in which an object has made contact with the part corresponding to the sterile region).

Subsequently, the medical observation apparatus 100 causes a notification of the notification content corresponding to the determination result of the "state related to the relationship between the part corresponding to the sterile region and an object" to be issued (notification control process). As described above, for example, the medical observation apparatus 100 issues a notification of the notification content by a visual notification, an aural notification, a combination of the two, or the like.

By performing the above state determination process and the above notification control process as the process related to the state notification method according to the present embodiment, a medical personnel member such as the surgeon is able to recognize that one is coming close to the part corresponding to the sterile region in the medical observation apparatus 100. Thus, by performing the process related to the state notification method according to the present embodiment, during surgery, a medical personnel member such as the surgeon is able to preemptively avoid accidentally making contact with the medical sterile cover by a site whose sterile state is not ensured, such as one's head.

Consequently, by performing the process related to the state notification method according to the present embodiment, contact with the sterile region by a medical personnel member can be preemptively avoided.

Also, by preemptively avoiding contact with the sterile region by a medical personnel member, the situation of re-covering the medical observation apparatus 100 with a new medical sterile cover is also reduced. Thus, by performing the process related to the state notification method according to the present embodiment, reductions in surgical efficiency are prevented, and moreover, increases in the costs associated with the medical sterile cover are also prevented.

Furthermore, in the case in which the medical observation apparatus 100 determines the contacting state and issues a notification of the contacting state, a medical personnel member such as the surgeon is able to recognize that one has made contact with the part corresponding to the sterile region in the medical observation apparatus 100. Thus, by performing the process related to the state notification method according to the present embodiment, a situation in which the sterile state of the medical observation apparatus 100 ceases to be ensured without the knowledge of the medical personnel member can be prevented reliably.

Note that in the case in which the medical observation apparatus included in the medical observation system 1000 is an electronic imaging medical observation apparatus as illustrated in FIG. 1, a user who uses the electronic imaging medical observation apparatus (for example, a medical personnel member such as a surgeon or a surgeon's assistant) is not required to peer into an eyepiece lens included in an optical microscope like in the case of using an optical medical observation apparatus, and thus it is possible to move the position of the imaging device more freely. For this reason, in the case in which the medical observation apparatus included in the medical observation system 1000 is an electronic imaging medical observation apparatus, the possibility of a site whose sterile state is not ensured on a medical personnel member making contact with the sterile region is conceivably higher than the case in which the medical observation apparatus included in the medical observation system 1000 is an optical medical observation apparatus.

As described above, in the case of performing the process related to the state notification method according to the present embodiment, a medical personnel member such as the surgeon is able to recognize each of approaching the part corresponding to the sterile region in the medical observation apparatus 100, and making contact with the part corresponding to the sterile region in the medical observation apparatus 100. Thus, even in the case in which the medical observation apparatus included in the medical observation system 1000 is an electronic imaging medical observation apparatus as illustrated in FIG. 1, during surgery, a medical personnel member such as the surgeon is able to preemptively avoid accidentally making contact with the medical sterile cover by a site whose sterile state is not ensured, such as one's head. Also, even in the hypothetical case in which the medical personnel member accidentally makes contact with the medical sterile cover, a situation in which the sterile state of the medical observation apparatus 100 ceases to be ensured without the knowledge of the medical personnel member can be prevented reliably.

[2-2] Example of Process Related to State Notification Method According to Present Embodiment Next, the process related to the state notification method according to the present embodiment will be described more specifically.

[2-2-1] First Example of Process Related to State Notification Method: Process in Case of Issuing Notification of Approaching State (1) State Determination Process The medical observation apparatus 100 determines if the approaching state exists, on the basis of the "the distance between the part corresponding to the sterile region and an object existing in the periphery of the part corresponding to the sterile region". In the medical observation apparatus 100, the determination process is performed by the determination section 176, for example. Hereinafter, the process of determining if the approaching state exists may be designated the "process of determining the approaching state" in some cases.

For example, from a detection result obtained from each of multiple distance sensors, such as the distance sensors DS1, DS2, DS3, and so on illustrated in FIG. 4, the medical observation apparatus 100 specifies "the distance between the part corresponding to the sterile region and an object existing in the periphery of the part corresponding to the sterile region". Computations related to the specification of the distance may be performed by the distance sensors, or by a processor (not illustrated) that functions as the control section 162. Hereinafter, "the distance between the part corresponding to the sterile region and an object existing in the periphery of the part corresponding to the sterile region" will be designated simply "the distance to the object" in some cases.

The medical observation apparatus 100 determines if the approaching state exists by comparing the specified distance to the object to a set first threshold value. The set first threshold value may be a fixed value set in advance, such as 50 [mm], for example, or a variable value that is changeable on the basis of an operation or the like by a person who uses the medical observation system 1000, such as a medical personnel member.

In the case in which the distance to the object is less than or equal to the set first threshold value (or in the case in which the distance is less than the first threshold value), the medical observation apparatus 100 determines that the approaching state exists. Also, in the case in which the distance to the object is greater than the set first threshold value (or in the case in which the distance is equal to or greater than the first threshold value), the medical observation apparatus 100 does not determine that the approaching state exists.

In addition, for example, the medical observation apparatus 100 may also perform the process of determining the approaching state on the basis of the operating state of the medical observation apparatus 100.

As described later, in the case in which the approaching state is determined to exist, the medical observation apparatus 100 causes a notification of the approaching state to be issued. In other words, "the medical observation apparatus 100 determining whether to perform the process of determining the approaching state on the basis of the operating state of the medical observation apparatus 100" corresponds to "the medical observation apparatus 100 determining whether a state of issuing a notification exists on the basis of the operating state of the medical observation apparatus 100".

To give one example, the medical observation apparatus 100 performs the process of determining the approaching state in the case in which the operating state of the medical observation apparatus 100 is the locked state in which the position and the attitude of the imaging device 106 are locked. For example, in the case in which the operating mode of the arm 104 is the locked mode, the medical observation apparatus 100 treats the operating state as being the locked state, and performs the process of determining the approaching state.

In addition, the medical observation apparatus 100 does not perform the process of determining the approaching state in the case in which the operating state of the medical observation apparatus 100 is not the locked state. For example, in the case in which the operating mode of the arm 104 is an operating mode other than the locked mode, such as in the case in which the operating mode of the arm 104 is in the free mode, the medical observation apparatus 100 treats the operating state as not being the locked state, and does not perform the process of determining the approaching state.

Herein, in the case in which the operating mode of the arm 104 is an operating mode other than the locked mode, such as in the case in which the operating mode of the arm 104 is the free mode, there is a high likelihood that a medical personnel member such as the surgeon will intentionally touch and operate the medical observation apparatus 100. Also, when the medical personnel member attempts to touch the medical observation apparatus 100 intentionally, if a notification of the approaching state is issued, there is a risk that the medical personnel member may feel annoyed by the notification of the approaching state.

As above, by having the medical observation apparatus 100 not perform the process of determining the approaching state in the case in which the operating state of the medical observation apparatus 100 is not the locked state, the notification of the approaching state is prevented from being issued when a medical personnel member attempts to touch the medical observation apparatus 100 intentionally. Thus, by having the medical observation apparatus 100 not perform the process of determining the approaching state in the case in which the operating state of the medical observation apparatus 100 is not the locked state, convenience for the medical personnel member can be improved.

(2) Notification Control Process

The medical observation apparatus 100 causes a notification of the approaching state to be issued on the basis of a determination result of the approaching state in the state determination process according to the first example indicated in (1) above. In the medical observation apparatus 100, the notification control process is performed by the notification control section 178 (or the display control section 174), for example.

The medical observation apparatus 100 causes a notification of the approaching state to be issued in the case in which the approaching state is determined to exist in the state determination process according to the first example indicated in (1) above. Also, for example, the medical observation apparatus 100 does not cause any notification to be issued in the case in which the approaching state is not determined to exist in the state determination process according to the first example indicated in (1) above. Note that in the case in which the approaching state is not determined to exist in the state determination process according to the first example indicated in (1) above, obviously it is also possible for the medical observation apparatus 100 to issue a notification indicating that the state is not the approaching state.

For example, by controlling one or both of the notification device included in the notification section 160 and an external notification device such as the display apparatus 200, the medical observation apparatus 100 causes a notification of the approaching state to be issued visually, aurally, by a combination of the two, or the like. Note that it is also possible for the medical observation apparatus 100 to issue a notification of the approaching state by an arbitrary notification method which is perceivable by a medical personnel member, such as by inducing vibration in a vibration device (one example of an external notification device) worn by a medical personnel member such as the surgeon.

Figure 7:
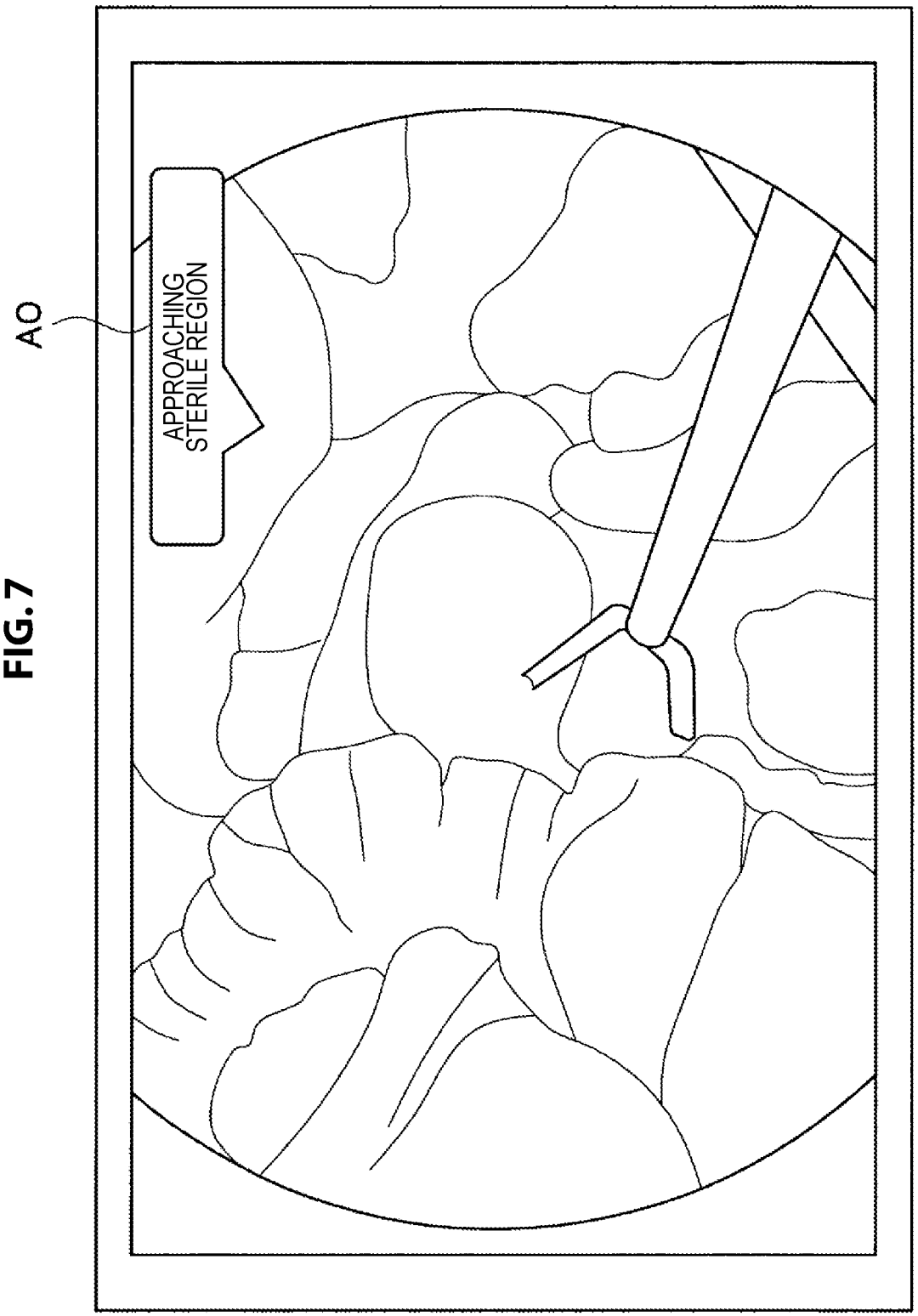
FIG. 7 is an explanatory diagram for describing an example of a process related to a state notification method according to the present embodiment.

FIG. 7 is an explanatory diagram for describing an example of a process related to the state notification method according to the present embodiment, and illustrates an example in which a notification of the approaching state is issued visually.

As illustrated in FIG. 7, for example, the medical observation apparatus 100 causes a notification of the approaching state to be issued by causing a notification object AO indicating the approaching state to be displayed on the display screen of the display apparatus 200.

Note that the example of causing a notification of the approaching state to be issued visually is not limited to the example illustrated in FIG. 7. For example, as described above, it is possible for the medical observation apparatus 100 to cause a notification of the approaching state to be issued by causing an icon (one example of an image) indicating the approaching state to be displayed, by causing an indicator lamp that lights up to indicate the approaching state to be turned on, or the like.

By performing the state determination process according to the first example indicated in (1) above and the notification control process according to the first example indicated in (2) above, for example, the medical observation apparatus 100 determines the approaching state and causes a notification of the approaching state to be issued.

Figure 8:
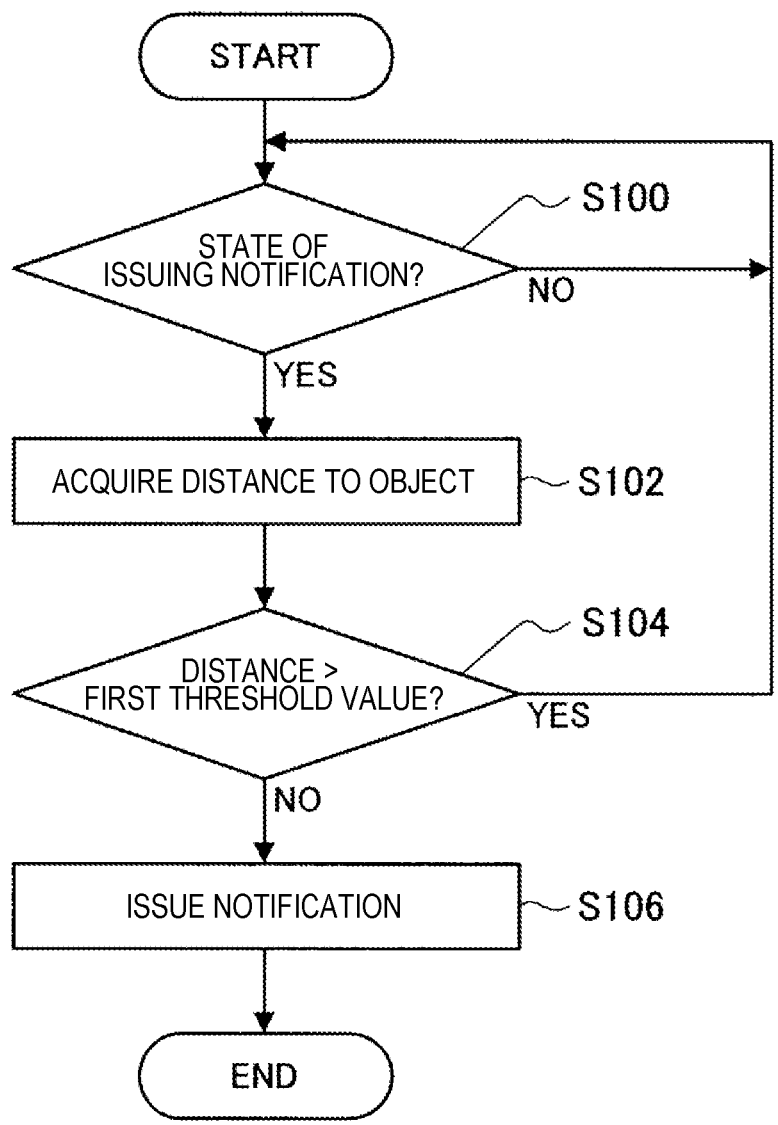
FIG. 8 is a flowchart illustrating an example of a process related to the state notification method according to the present embodiment.

Next, an example of the process related to the state notification method according to the first example will be described. FIG. 8 is a flowchart illustrating an example of the process related to the state notification method according to the present embodiment, and illustrates an example of the process in the case in which the medical observation apparatus 100 issues a notification of the approaching state.

The medical observation apparatus 100 determines whether or not a state of issuing a notification exists (S100). For example, the medical observation apparatus 100 determines that the state of issuing a notification exists in the case in which the operating state of the medical observation apparatus 100 is the locked state. As described above, the process of step S100 corresponds to a process of the medical observation apparatus 100 determining whether to perform the process of determining the approaching state on the basis of the operating state of the medical observation apparatus 100.

In the case of not determining that a state of issuing a notification exists in step S100, the medical observation apparatus 100 does not advance the process until determining that the state of issuing a notification exists.

Also, in the case of determining that the state of issuing a notification exists in step S100, the medical observation apparatus 100 acquires the distance to the object (S102). Herein, the acquisition of the distance to the object in step S102 includes "obtaining the distance on the basis of the most recently detected detection result from among the distance detection results detected periodically/non-periodically by one or multiple distance sensors" (one example of a passive acquisition of distance), and "causing one or multiple distance sensors to operate by a processor (not illustrated) that functions as the control section 162 or the like, and obtaining the distance on the basis of a detection result obtained as a result" (one example of an active acquisition of distance). Also, as described above, computations related to the specification of the distance may be performed by the distance sensors, or by the processor (not illustrated) that functions as the control section 162.

The medical observation apparatus 100 determines whether or not the distance acquired in step S102 is greater than a first threshold value (S104). Note that in step S104, the medical observation apparatus 100 may also determine whether or not the distance acquired in step S102 is equal to or greater than the first threshold value.

In the case of determining in step S104 that the acquired distance is greater than the first threshold value, the medical observation apparatus 100 repeats the process from step S100.

Also, in the case of not determining in step S104 that the acquired distance is greater than the first threshold value, the medical observation apparatus 100 issues a notification of the approaching state by controlling one or both of the notification device included in the notification section 160 and an external notification device such as the display apparatus 200 (S106).

In the case of issuing a notification of the approaching state, the medical observation apparatus 100 performs the process illustrated in FIG. 8, for example. Note that the process in the case of issuing a notification of the approaching state obviously is not limited to the example illustrated in FIG. 8.

[2-2-2] Second Example of Process Related to State Notification Method: Process in Case of Issuing Notification of Approaching State and Contacting State
(I) State Determination Process The medical observation apparatus 100 determines each of the approaching state and the contacting state. In other words, in the state determination process according to the second example, in addition to the state determination process according to the first example indicated in (1) above, it is additionally determined if the contacting state exists. In the medical observation apparatus 100, the determination process is performed by the determination section 176, for example.

Similarly to the state determination process according to the first example indicated in (1) above, the medical observation apparatus 100 determines the approaching state on the basis of the distance to the object. Also, similarly to the state determination process according to the first example indicated in (1) above, the medical observation apparatus 100 may also perform the process of determining the approaching state on the basis of the operating state of the medical observation apparatus 100.

Additionally, the medical observation apparatus 100 determines the contacting state on the basis of a detection result from one or multiple contact sensors provided in the part corresponding to the sterile region, like the strain gauges SS1, SS2, and so on illustrated in FIG. 5, for example.

The medical observation apparatus 100 determines if the contacting state exists by comparing a detection value indicated by the detection results from the contact sensors to a set second threshold value. The detection value indicated by the detection results from the contact sensors may be, for example, a voltage difference produced in response to strain (one example of a detection value in the case in which the contact sensors are strain gauges), or an acceleration (one example of a detection value in the case in which the contact sensors are acceleration sensors). The set second threshold value may be a fixed value set in advance, or a variable value that is changeable on the basis of an operation or the like by a person who uses the medical observation system 1000, such as a medical personnel member.

In the case in which the detection value indicated by the detection results from the contact sensors is greater than the set second threshold value (or in the case in which the detection value is equal to or greater than the second threshold value), the medical observation apparatus 100 determines that the contacting state exists. Also, in the case in which the detection value indicated by the detection results from the contact sensors is less than or equal to the set second threshold value (or in the case in which the detection value is less than the second threshold value), the medical observation apparatus 100 does not determine that the contacting state exists.

In addition, for example, the medical observation apparatus 100 may also perform the process of determining the contacting state on the basis of the operating state of the medical observation apparatus 100.

As described later, in the case in which the contacting state is determined to exist, the medical observation apparatus 100 causes a notification of the contacting state to be issued. In other words, "the medical observation apparatus 100 determining whether to perform the process of determining the contacting state on the basis of the operating state of the medical observation apparatus 100" corresponds to "the medical observation apparatus 100 determining whether a state of issuing a notification exists on the basis of the operating state of the medical observation apparatus 100".

To give one example, the medical observation apparatus 100 performs the process of determining the contacting state in the case in which the operating state of the medical observation apparatus 100 is the locked state. For example, in the case in which the operating mode of the arm 104 is the locked mode, the medical observation apparatus 100 treats the operating state as being the locked state, and performs the process of determining the contacting state.

In addition, the medical observation apparatus 100 does not perform the process of determining the contacting state in the case in which the operating state of the medical observation apparatus 100 is not the locked state. For example, in the case in which the operating mode of the arm 104 is an operating mode other than the locked mode, such as in the case in which the operating mode of the arm 104 is in the free mode, the medical observation apparatus 100 does not perform the process of determining the contacting state.

As described above, in the case in which the operating mode of the arm 104 is an operating mode other than the locked mode, there is a high likelihood that a medical personnel member such as the surgeon will intentionally touch and operate the medical observation apparatus 100. Also, when the medical personnel member attempts to touch the medical observation apparatus 100 intentionally, if a notification of the contacting state is issued, there is a risk that the medical personnel member may feel annoyed by the notification of the contacting state.

As above, by having the medical observation apparatus 100 not perform the process of determining the contacting state in the case in which the operating state of the medical observation apparatus 100 is not the locked state, the notification of the contacting state is prevented from being issued when a medical personnel member attempts to touch the medical observation apparatus 100 intentionally. Thus, by having the medical observation apparatus 100 not perform the process of determining the contacting state in the case in which the operating state of the medical observation apparatus 100 is not the locked state, convenience for the medical personnel member can be improved.

(II) Notification Control Process

The medical observation apparatus 100 causes a notification of each of the approaching state and the contacting state to be issued. In other words, in the state determination process according to the second example, in addition to the notification control process according to the first example indicated in (2) above, a notification of the approaching state is made to be issued. In the medical observation apparatus 100, the notification control process is performed by the notification control section 178 (or the display control section 174), for example.

Similarly to the notification control process according to the first example indicated in (2) above, the medical observation apparatus 100 causes a notification of the approaching state to be issued on the basis of a determination result of the approaching state in the state determination process according to the second example indicated in (I) above.

The medical observation apparatus 100 causes a notification of the contacting state to be issued in the case in which the contacting state is determined to exist in the state determination process according to the second example indicated in (I) above. Also, for example, the medical observation apparatus 100 does not cause any notification to be issued in the case in which the contacting state is not determined to exist in the state determination process according to the second example indicated in (I) above. Note that in the case in which the contacting state is not determined to exist in the state determination process according to the second example indicated in (I) above, obviously it is also possible for the medical observation apparatus 100 to issue a notification indicating that the state is not the contacting state.

For example, by controlling one or both of the notification device included in the notification section 160 and an external notification device such as the display apparatus 200, the medical observation apparatus 100 causes a notification of the contacting state to be issued visually, aurally, by a combination of the two, or the like. Note that it is also possible for the medical observation apparatus 100 to issue a notification of the contacting state by an arbitrary notification method which is recognizable by a medical personnel member, such as by inducing vibration in a vibration device (one example of an external notification device) worn by a medical personnel member such as the surgeon. For example, in the case of issuing a notification of each of the approaching state and the contacting state haptically by vibration, the medical observation apparatus 100 changes the way in which the vibration is induced.

Figure 9:
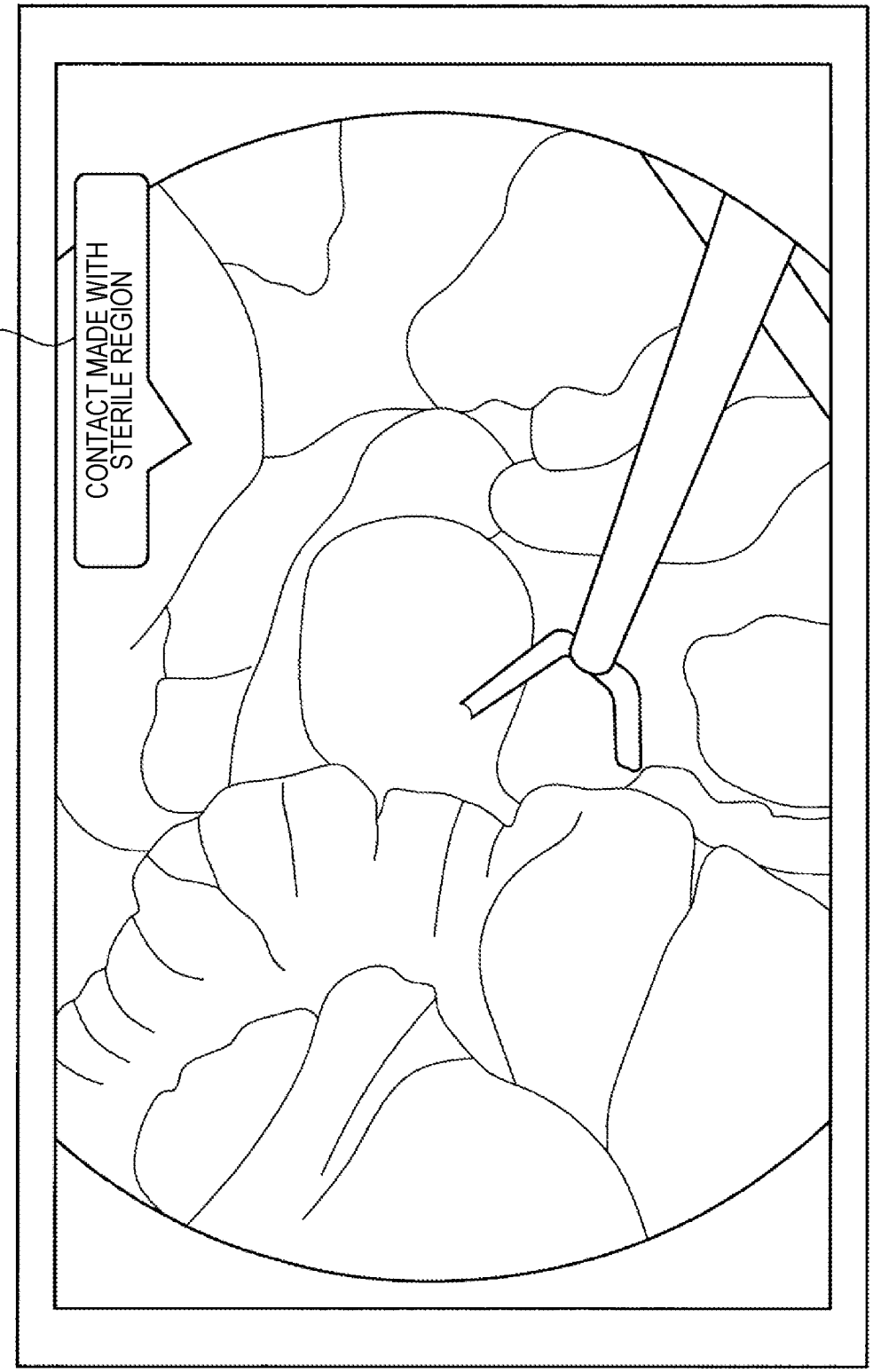
FIG. 9 is an explanatory diagram for describing another example of a process related to the state notification method according to the present embodiment.

FIG. 9 is an explanatory diagram for describing another example of a process related to the state notification method according to the present embodiment, and illustrates an example in which a notification of the contacting state is issued visually.

As illustrated in FIG. 9, for example, the medical observation apparatus 100 causes a notification of the contacting state to be issued by causing a notification object AO indicating the contacting state to be displayed on the display screen of the display apparatus 200.

Note that the example of causing a notification of the contacting state to be issued visually is not limited to the example illustrated in FIG. 9.

For example, as described above, it is possible for the medical observation apparatus 100 to cause a notification of the contacting state to be issued by causing an icon (one example of an image) indicating the contacting state to be displayed, by causing an indicator lamp that lights up to indicate the contacting state to be turned on, or the like.

Additionally, in the case of issuing a notification of the contacting state visually, the medical observation apparatus 100 may also visually indicate the part corresponding to the sterile region that the object has come into contact with. For example, the medical observation apparatus 100 visually indicates the part corresponding to the sterile region that the object has come into contact with by "applying color to the part corresponding to the sterile region that the object has come into contact with on a 3D model of the medical observation apparatus 100". The part corresponding to the sterile region that the object has come into contact with is estimated according to the position where the contact sensors corresponding to the detection values used when determining the contacting state are provided, for example.

By performing the state determination process according to the second example indicated in (I) above and the notification control process according to the second example indicated in (II) above, for example, the medical observation apparatus 100 determines each of the approaching state and the contacting state, and causes notifications of the determined states to be issued.

Next, an example of the process related to the state notification method according to the second example will be described.

In the case of issuing a notification of the approaching state, the medical observation apparatus 100 performs the process illustrated in FIG. 8, for example.

FIG. 10 is a flowchart illustrating another example of the process related to the state notification method according to the present embodiment, and illustrates an example of the process in the case in which the medical observation apparatus 100 issues a notification of the contacting state. FIG. 10 illustrates an example of a process in the case in which the contact sensors are strain gauges.

As in step S100 in FIG. 8, the medical observation apparatus 100 determines whether or not a state of issuing a notification exists (S200). For example, the medical observation apparatus 100 determines that the state of issuing a notification exists in the case in which the operating state of the medical observation apparatus 100 is the locked state. As described above, the process of step S200 corresponds to a process of the medical observation apparatus 100 determining whether to perform the process of determining the contacting state on the basis of the operating state of the medical observation apparatus 100.

In the case of not determining that a state of issuing a notification exists in step S200, the medical observation apparatus 100 does not advance the process until determining that the state of issuing a notification exists.

Also, in the case of determining that the state of issuing a notification exists in step S200, the medical observation apparatus 100 acquires a strain detection value (S202). Herein, the acquisition of strain detection values in step S202 includes, for example, "obtaining the most recently detected detection value from among detection values indicating strain detection results continually detected by one or multiple strain gauges" (one example of a passive acquisition of the strain detection value), and "causing one or multiple strain gauges to operate by a processor (not illustrated) that functions as the control section 162 or the like, and obtaining a detection value indicating the detection result obtained as a result" (one example of an active acquisition of the strain detection value).

The medical observation apparatus 100 determines whether or not the strain detection value acquired in step S202 is greater than a second threshold value (S204). Note that in step S204, the medical observation apparatus 100 may also determine whether or not the strain detection value acquired in step S202 is equal to or greater than the second threshold value.

In the case of not determining in step S204 that the acquired strain detection value is greater than the second threshold value, the medical observation apparatus 100 repeats the process from step S200.

Also, in the case of determining in step S204 that the acquired strain detection value is greater than the second threshold value, the medical observation apparatus 100 issues a notification of the contacting state by controlling one or both of the notification device included in the notification section 160 and an external notification device such as the display apparatus 200 (S206).

In the case of issuing a notification of the contacting state, the medical observation apparatus 100 performs the process illustrated in FIG. 10, for example. Note that the process in the case of issuing a notification of the contacting state obviously is not limited to the example illustrated in FIG. 10.

[2-2-3] Third Example of Process Related to State Notification Method: Process in Case of Issuing Notification of Contacting State Note that the process related to the state notification method according to the present embodiment is not limited to the process according to the first example indicated in [2-2-1] above and the process according to the second example indicated in [2-2-2] above. For example, the medical observation apparatus 100 may determine the contacting state, and cause a notification of the determined contacting state to be issued.

(Program According to Present Embodiment)

By having a program (for example, a program capable of executing the process related to the state notification method according to the present embodiment, such as the state determination process and the notification control process, for example) for causing a computer system to function as the medical observation apparatus according to the present embodiment (or the control apparatus according to the present embodiment) be executed by a processor or the like in the computer system, contact with the sterile region by a medical personnel member can be preemptively deterred. Herein, the computer system according to the present embodiment includes a single computer or multiple computers. A series of processes related to the state notification method according to the present embodiment is performed by the computer system according to the present embodiment.

Additionally, by having the program for causing a computer system to function as the medical observation apparatus according to the present embodiment (or the control apparatus according to the present embodiment) be executed by a processor or the like in the computer system, the effects exhibited by the display realized by the process related to the state notification method according to the present embodiment described above can be exhibited.

It should be understood by those skilled in the art that various modifications, combinations, sub-combinations and alterations may occur depending on design requirements and other factors insofar as they are within the scope of the appended claims or the equivalents thereof.

For example, although the above indicates that a program (computer program) for causing a computer system to function as the medical observation apparatus according to the present embodiment is provided, in the present embodiment, the above program may also be provided in conjunction with a recording medium on which the above program is stored.

The configuration described above illustrates one example of the present embodiment, and rightfully belongs to the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1) A medical observation apparatus including:
a determination section configured to determine, on a basis of distance between a part corresponding to a sterile region and an object existing in a periphery of the part corresponding to the sterile region, if an approaching state in which an object is approaching the part corresponding to the sterile region exists; and a notification control section configured to cause a notification of the approaching state to be issued, on a basis of a determination result of the approaching state.

(2) The medical observation apparatus according to (1), further including:

an imaging section that includes an imaging device configured to image an observation target, in which the imaging device is supported by an arm including a plurality of links joined to each other by one or a plurality of joint sections, and the part corresponding to the sterile region is a part including the imaging device and at least a portion of the arm.

(3) The medical observation apparatus according to (2), in which the determination section performs a process of determining the approaching state on a basis of an operating state of the medical observation apparatus.

(4) The medical observation apparatus according to (3), in which the determination section performs the process of determining the approaching state in a case in which the operating state of the medical observation apparatus is a locked state in which a position and an attitude of the imaging device are locked, and does not perform the process of determining the approaching state in a case in which the operating state of the medical observation apparatus is not the locked state.

(5) The medical observation apparatus according to any one of (1) to (4), in which the part corresponding to the sterile region is a part covered by a medical sterile cover.

(6) The medical observation apparatus according to any one of (1) to (5), in which the determination section determines that the approaching state exists in a case in which the distance is less than or equal to a set first threshold value, or in a case in which the distance is less than the first threshold value.

(7) The medical observation apparatus according to any one of (1) to (6), in which the distance is detected by one or a plurality of distance sensors provided in the part corresponding to the sterile region.

(8) The medical observation apparatus according to any one of (1) to (7), in which the notification control section causes a notification of the approaching state to be issued visually.

(9) The medical observation apparatus according to any one of (1) to (8), in which the notification control section causes a notification of the approaching state to be issued aurally.

(10) The medical observation apparatus according to any one of (1) to (9), in which the determination section additionally determines a contacting state in which an object has made contact with the part corresponding to the sterile region, on a basis of a detection result of one or a plurality of contact sensors provided in the part corresponding to the sterile region, and the notification control section additionally causes a notification of the contacting state to be issued, on a basis of a determination result of the contacting state.

(11) The medical observation apparatus according to (10), in which the determination section performs a process of determining the contacting state on a basis of an operating state of the medical observation apparatus.

(12) The medical observation apparatus according to (10) or (11), in which the determination section determines that the contacting state exists in a case in which a detection value indicated by a detection result of the one or plurality of contact sensors is greater than a set second threshold value, or in a case in which the detection value is equal to or greater than the second threshold value.

(13) The medical observation apparatus according to any one of (10) to (12), in which the notification control section causes a notification of the contacting state to be issued visually.

(14) The medical observation apparatus according to any one of (10) to (13), in which the notification control section causes a notification of the contacting state to be issued aurally.

(15) The medical observation apparatus according to any one of (1) to (14), further including:

a notification section that includes a notification device configured to issue a notification of notification content.

(16) A state notification method executed by a medical observation apparatus, the state notification method including:

determining, on a basis of distance between a part corresponding to a sterile region and an object existing in a periphery of the part corresponding to the sterile region, if an approaching state in which an object is approaching the part corresponding to the sterile region exists; and causing a notification of the approaching state to be issued, on a basis of a determination result of the approaching state.

What is claimed is:

1. A medical observation apparatus comprising:
   a determination section configured to determine, on a basis of distance between a part corresponding to a sterile region and an object existing in a periphery of the part corresponding to the sterile region, if an approaching state in which an object is approaching the part corresponding to the sterile region exists; and
   a notification control section configured to cause a notification of the approaching state to be issued, on a basis of a determination result of the approaching state.

2. The medical observation apparatus according to claim 1, further comprising:
   an imaging section that includes an imaging device configured to image an observation target, wherein
   the imaging device is supported by an arm including a plurality of links joined to each other by one or a plurality of joint sections, and
   the part corresponding to the sterile region is a part including the imaging device and at least a portion of the arm.

3. The medical observation apparatus according to claim 2, wherein
   the determination section performs a process of determining the approaching state on a basis of an operating state of the medical observation apparatus.

4. The medical observation apparatus according to claim 3, wherein
   the determination section
   performs the process of determining the approaching state in a case in which the operating state of the medical observation apparatus is a locked state in which a position and an attitude of the imaging device are locked, and
does not perform the process of determining the approaching state in a case in which the operating state of the medical observation apparatus is not the locked state.

5. The medical observation apparatus according to claim 1, wherein
the part corresponding to the sterile region is a part covered by a medical sterile cover.

6. The medical observation apparatus according to claim 1, wherein
the determination section determines that the approaching state exists in a case in which the distance is less than or equal to a set first threshold value, or in a case in which the distance is less than the first threshold value.

7. The medical observation apparatus according to claim 1, wherein
the distance is detected by one or a plurality of distance sensors provided in the part corresponding to the sterile region.

8. The medical observation apparatus according to claim 1, wherein
the notification control section causes a notification of the approaching state to be issued visually.

9. The medical observation apparatus according to claim 1, wherein
the notification control section causes a notification of the approaching state to be issued aurally.

10. The medical observation apparatus according to claim 1, wherein
the determination section additionally determines a contacting state in which an object has made contact with the part corresponding to the sterile region, on a basis of a detection result of one or a plurality of contact sensors provided in the part corresponding to the sterile region, and
the notification control section additionally causes a notification of the contacting state to be issued, on a basis of a determination result of the contacting state.

11. The medical observation apparatus according to claim 10, wherein
the determination section performs a process of determining the contacting state on a basis of an operating state of the medical observation apparatus.

12. The medical observation apparatus according to claim 10, wherein
the determination section determines that the contacting state exists in a case in which a detection value indicated by a detection result of the one or plurality of contact sensors is greater than a set second threshold value, or in a case in which the detection value is equal to or greater than the second threshold value.

13. The medical observation apparatus according to claim 10, wherein
the notification control section causes a notification of the contacting state to be issued visually.

14. The medical observation apparatus according to claim 10, wherein
the notification control section causes a notification of the contacting state to be issued aurally.

15. The medical observation apparatus according to claim 1, further comprising:
a notification section that includes a notification device configured to issue a notification of notification content.

16. A state notification method executed by a medical observation apparatus, the state notification method comprising:
determining, on a basis of distance between a part corresponding to a sterile region and an object existing in a periphery of the part corresponding to the sterile region, if an approaching state in which an object is approaching the part corresponding to the sterile region exists; and
causing a notification of the approaching state to be issued, on a basis of a determination result of the approaching state.

\* \* \* \* \*